US012784892B2

(12) United States Patent
McDonough

(10) Patent No.: US 12,784,892 B2
(45) Date of Patent: Nov. 3, 2026

(54) BRAIN STATE RULE GENERATION AND SCORING SYSTEM AND METHOD

(71) Applicant: Mark McDonough, Manchester, MA (US)

(72) Inventor: Mark McDonough, Manchester, MA (US)

( * ) Notice: Subject to any disclaimer, the term of this patent is extended or adjusted under 35 U.S.C. 154(b) by 126 days.

(21) Appl. No.: 18/305,796

(22) Filed: Apr. 24, 2023

(65) Prior Publication Data

US 2024/0355452 A1 Oct. 24, 2024

(51) Int. Cl.
*G06Q 10/00* (2026.01)
*G16H 20/70* (2018.01)
*G16H 50/70* (2018.01)

(52) U.S. Cl.
CPC ............ *G16H 20/70* (2018.01); *G16H 50/70* (2018.01)

(58) Field of Classification Search
CPC .............................. G16H 20/70; G16H 50/70
See application file for complete search history.

(56) References Cited

U.S. PATENT DOCUMENTS 5,363,858 A * 11/1994 Farwell .................. A61B 5/374
607/139
11,056,223 B1 * 7/2021 Ahmad ................ A61B 5/6898
11,763,919 B1 * 9/2023 Jain ........................ G16H 10/20
715/221
11,929,162 B1 * 3/2024 McDonough .......... A61B 5/372
2009/0030945 A1 * 1/2009 Miller ................... G06F 16/248
2015/0351655 A1 12/2015 Coleman
2021/0304870 A1 * 9/2021 Kaplan .................. G16H 20/70
2021/0308413 A1 * 10/2021 Pierne ................... A61M 21/02
2022/0218942 A1 * 7/2022 Jain ....................... A61M 21/02
2022/0262518 A1 * 8/2022 Navani .................. G16H 50/20
2022/0327624 A1 * 10/2022 Takatkah ............... G06Q 40/06
2023/0282080 A1 * 9/2023 Mulliken ............... A61B 5/168
340/573.1

(Continued)

OTHER PUBLICATIONS

Riba et al., "Effects of the South American psychoactive beverage ayahuasca on regional brain electrical activity in humans: a functional neuroimaging study using low-resolution electromagnetic tomography", published Jun. 2004; http://psychemical.weebly.com/uploads/9/9/1/6/991662/effects_of_ayahuasca_on_regional_brain_electrical_activity.pdf [retrieved Jul. 24, 2023].

(Continued)

*Primary Examiner* — Rajesh Khattar
(74) *Attorney, Agent, or Firm* — Plumsea Law Group, LLC; Aisha A. Moinuddin

(57) ABSTRACT

Methods and systems for intelligent development of protocols that promote a specific target brain state and the scoring of brainwave activity. In one embodiment, datasets describing performance of different meditation styles can be used to automatically create brain state protocols that, when implemented, can guide a user's meditation experience toward a selected meditation style. In another embodiment, users can submit their brain data to custom-create new brain state protocols that are tailored to their desired brain states and/or neuropsychological profiles. Furthermore, the proposed embodiments offer a brain state depth scoring process that adapts to the target brain state that is being practiced.

20 Claims, 19 Drawing Sheets

(56) References Cited

U.S. PATENT DOCUMENTS

2024/0350053 A1* 10/2024 Shankar ............... A61B 5/7278

OTHER PUBLICATIONS

Schenberg et al., "Acute Biphasic Effects of Ayahuasca", published Sep. 2015; https://www.ncbi.nlm.nih.gov/pmc/articles/PMC4589238/pdf/pone.0137202.pdf [retrieved Jul. 10, 2023].
Amihai et al., "Arousal vs. Relaxation: A Comparison of the Neurophysiological and Cognitive Correlates of Vajrayana and Theravada Meditative Practices", published Jul. 2014; https://journals.plos.org/plosone/article/file?id=10.1371/journal.pone.0102990&type=printable [retrieved Jul. 10, 2023].
Dor-Ziderman et al., "Mindfulness-induced selflessness: a MEG neurophenomenological study", published Sep. 2013; https://www.researchgate.net/profile/Joseph-Glicksohn/publication/257075456_Mindfulness-induced_selflessness_A_MEG_neurophenomenological_study/links/00463524ced8b61a6f000000/Mindfulness-induced-selflessness-A-MEG-neurophenomenological-study.pdf [retrieved Jul. 10, 2023].
Hinterberger et al., "Decreased electrophysiological activity represents the conscious state of emptiness in meditation", published Feb. 2014; https://www.readcube.com/articles/10.3389/fpsyg.2014.00099 [retrieved Jul. 10, 2023].
Huang et al., "EEG dynamics of experienced Zen meditation practitioners probed by complexity index and spectral measure," published Jul. 2009; https://www.tandfonline.com/doi/full/10.1080/03091900802602677 [retrieved Aug. 3, 2023].
Haiteng, et al., "Brain-Heart interactions underlying traditional Tibetan Buddhist meditation", published Jun. 2019; https://academic.oup.com/cercor/article/30/2/439/5510041 [retrieved Aug. 3, 2023].
Josipovic, Zoran, "Neural correlates of nondual awareness in meditation", published Sep. 2013; https://meditationforteachers.weebly.com/uploads/1/0/7/9/107957965/neuralcorrelatesofnon-dualawarenessmeditation.pdf [retrieved Jul. 24, 2023].
Kakumanu et al., "Dissociating meditation proficiency and experience dependent EEG changes during traditional Vipassana meditation practice", published Mar. 2018; https://www.sciencedirect.com/science/article/abs/pii/S0301051118301728?via%3Dihub [retrieved Aug. 3, 2023].
Kopal et al., "Complex continuous wavelet coherence for EEG microstates detection in insight and calm meditation", published Aug. 2014; https://praveted.info/files/kopal_vysata_burian_wavelet_meditation.pdf [retrieved Jul. 14, 2023].
Kozhevnikov et al., "The Importance of Generation Stage Yidam Practice in Vajrayana", published Mar. 2018; https://www.academia.edu/37974950/The_Importance_of_Generation_Stage_Yidam_Practice_in_Vajrayana [retrieved Aug. 3, 2023].
Lehmann et al., "Brain sources of EEG gamma frequency during volitionally meditation-induced, altered states of consciousness, and experience of the self", published Nov. 2001; https://www.sciencedirect.com/science/article/abs/pii/S0925492701001160 [retrieved Aug. 3, 2023].
Lo et al., "Spatially Nonlinear Interdependence of Alpha-Oscillatory Neural Networks under Chan Meditation", published Dec. 2013; https://www.ncbi.nlm.nih.gov/pmc/articles/PMC3877605/pdf/ECAM2013-360371.pdf [retrieved Jul. 24, 2023].
Lo et al., "EEG alpha blocking correlated with perception of inner light during Zen meditation", published Feb. 2003; https://www.worldscientific.com/doi/abs/10.1142/S0192415X03001272 [retrieved Aug. 3, 2023].
Lutz et al., "Long-term meditators self-induce high-amplitude gamma synchrony during mental practice", published Nov. 2004; https://www.pnas.org/doi/epdf/10.1073/pnas.0407401101 [retrieved Jul. 24, 2023].
Murata et al., "Quantitative EEG study on Zen meditation (zaZen)", published Dec. 1994; https://onlinelibrary.wiley.com/doi/abs/10.1111/j.1440-1819.1994.tb03090.x [retrieved Aug. 8, 2023].
Schoenberg et al., "Mapping complex mind states: EEG neural substrates of meditative unified compassionate awareness", published Jan. 2018; https://www.sciencedirect.com/science/article/abs/pii/S1053810017303069 [retrieved Aug. 3, 2023].
Schoenberg et al., "Mindful disintegration and the decomposition of self in healthy populations: Conception and preliminary study", published Oct. 2016; https://www.researchgate.net/publication/309549711_Mindful_Disintegration_and_the_Decomposition_of_Self_in_Healthy_Populations_Conception_and_Preliminary_Study [retrieved Aug. 15, 2023].
Beauregard et al., "Neural correlates of a mystical experience in Carmelite nuns", published Sep. 2006; https://institutpsychoneuro.com/wp-content/uploads/2015/08/Beauregard2006-Carmelites-fmri.pdf [retrieved Jul. 24, 2023].
Beauregard et al., "EEG activity in Carmelite nuns during a mystical experience", published Oct. 2008; https://institutpsychoneuro.com/wp-content/uploads/2015/08/Beauregard2008-Carmelite-EEG.pdf [retrieved Jul. 24, 2023].
Acosta-Urquidi, Juan, "QEEG Studies of the Acute Effects of the Visionary Tryptamine DMT", published Oct. 2015; https://cosmosandhistory.org/index.php/journal/article/view/495/861 [retrieved Jul. 24, 2023].
Acosta-Urquidi, Juan, "EEG studies of the acute effects of 5-MeO-DMT. WBAC, CDMX Jul. 27-29, 2018", Published Oct. 2018; https://www.researchgate.net/publication/328117125_EEG_studies_of_the_acute_effects_of_5-MeO-_DMT_WBAC_CDMX_July_27-29_2018 [retrieved Jul. 24, 2023].
Atasoy et al., "Connectome-harmonic decomposition of human brain activity reveals dynamical repertoire re-organization under LSD", published Dec. 2017; https://www.researchgate.net/publication/321742460_Connectome-harmonic_decomposition_of_human_brain_activity_reveals_dynamical_repertoire_re-organization_under_LSD [retrieved Jul. 24, 2023].
Austin, James H., "Zen and the brain: mutually illuminating topics", published Oct. 2013; https://www.ncbi.nlm.nih.gov/pmc/articles/PMC3807561/pdf/fpsyg-04-00784.pdf [retrieved Jul. 24, 2023].
Carhart-Harris et al., "Neural correlates of the LSD experience revealed by multimodal neuroimaging", published Apr. 2016; https://www.pnas.org/doi/epdf/10.1073/pnas.1518377113 [retrieved Jul. 24, 2023].
Berman et al., "EEG manifestations of nondual experiences in meditators", published Jan. 2015; https://www.sciencedirect.com/science/article/abs/pii/S1053810014001809?via%3Dihub [retrieved Aug. 3, 2023].
Lehmann et al., "Reduced functional connectivity between cortical sources in five meditation traditions detected with lagged coherence using EEG tomography", published Apr. 2012; https://www.zora.uzh.ch/id/eprint/61702/1/NeuroImage_60%5B2%5D_pages_1574-1586_%282012%29.pdf [retrieved Jul. 24, 2023].
Pennington et al., "EcoMeditation and emotional freedom techniques (EFT) produce elevated brain-wave patterns and states of consciousness", published May 2019; https://sf1e9bc00d3c409d9.jimcontent.com/download/version/1564522634/module/11604409177/name/EFT%20and%20Ecomeditation%20Enhance%20MM%20Patterns.pdf [retrieved Jul. 24, 2023].
Carhart-Harris et al., "Neural correlates of the psychedelic state as determined by fMRI studies with psilocybin", published Feb. 2012; https://www.pnas.org/doi/epdf/10.1073/pnas.1119598109 [retrieved Jul. 24, 2023].
Kometer et al., "Psilocybin-induced spiritual experiences and insightfulness are associated with synchronization of neuronal oscillations", published Aug. 2015; https://ia803203.us.archive.org/33/items/LSDMDMAPsilocybinInDerPsychotherapieSTUDIEN/Psilocybin-inducedSpiritualExperiencesAndInsightfulnessAreAssociatedWithSynchronizationOfNeuronalOscillations.pdf [retrieved Jul. 24, 2023].
Lebedev et al., "Finding the self by losing the self: Neural correlates of ego-dissolution under psilocybin", published May 2015; https://europepmc.org/backend/ptpmcrender.fcgi?accid=PMC6869189&blobtype=pdf [retrieved Jul. 24, 2023].

(56) References Cited

OTHER PUBLICATIONS

Muthukumaraswamy et al., "Broadband cortical desynchronization underlies the human psychedelic state", published Sep. 2013; https://www.ncbi.nlm.nih.gov/pmc/articles/PMC6618409/pdf/zns15171.pdf [retrieved Jul. 24, 2023].
Petri et al., "Homological scaffolds of brain functional networks", published Dec. 2014; https://royalsocietypublishing.org/doi/epdf/10.1098/rsif.2014.0873 [retrieved Jul. 24, 2023].
Roseman et al., "The effects of psilocybin and MDMA on between-network resting state functional connectivity in healthy volunteers", published May 2014; https://www.ncbi.nlm.nih.gov/pmc/articles/PMC4034428/pdf/fnhum-08-00204.pdf [retrieved Jul. 24, 2023].
Smigielski et al., "Characterization and prediction of acute and sustained response to psychedelic psilocybin in a mindfulness group retreat", published Oct. 2019; https://www.ncbi.nlm.nih.gov/pmc/articles/PMC6813317/pdf/41598_2019_Article_50612.pdf [retrieved Jul. 24, 2023].
Smigielski et al., "P300-mediated modulations in self-other processing under psychedelic psilocybin are related to connectedness and changed meaning: A window into the self-other overlap", published Aug. 2020; https://www.ncbi.nlm.nih.gov/pmc/articles/PMC7643385/pdf/HBM-41-4982.pdf [retrieved Jul. 24, 2023].
Smigielski et al., "Psilocybin-assisted mindfulness training modulates self-consciousness and brain default mode network connectivity with lasting effects", published Aug. 2019; https://www.sciencedirect.com/science/article/abs/pii/S1053811919302952 [retrieved Aug. 3, 2023].
Hankey, Alex, "Studies of advanced stages of meditation in the Tibetan Buddhist and Vedic traditions. I: a comparison of general changes", published Jul. 2006; https://www.ncbi.nlm.nih.gov/pmc/articles/PMC1697747/pdf/nel040.pdf [retrieved Jul. 24, 2023].
Josipovic, Zoran, "Duality and nonduality in meditation research", published Apr. 2010; https://www.sciencedirect.com/science/article/abs/pii/S105381001000070X [retrieved Aug. 3, 2023].
Josipovic, Zoran, "Freedom of the mind", published Aug. 2013; https://www.ncbi.nlm.nih.gov/pmc/articles/PMC3753556/pdf/fpsyg-04-00538.pdf [retrieved Jul. 24, 2023].
Wahbeh et al., "A Systematic Review of Transcendent States Across Meditation and Contemplative Traditions", published Jan. 2018; https://www.sciencedirect.com/science/article/abs/pii/S1550830717300460?via%3Dihub [retrieved Aug. 3, 2023].
Barrett et al., "Classic hallucinogens and mystical experiences: phenomenology and neural correlates", published Mar. 2017; https://www.ncbi.nlm.nih.gov/pmc/articles/PMC6707356/pdf/nihms-1044542.pdf [retrieved Jul. 24, 2023].
Carhart-Harris et al., "Serotonin and brain function: a tale of two receptors", published Sep. 2017; https://www.ncbi.nlm.nih.gov/pmc/articles/PMC5606297/pdf/10.1177_0269881117725915.pdf [retrieved Jul. 24, 2023].
Carhart-Harris et al., "REBUS and the anarchic brain: toward a unified model of the brain action of psychedelics", published Jul. 2019; https://www.ncbi.nlm.nih.gov/pmc/articles/PMC6588209/pdf/pr.118.017160.pdf [retrieved Jul. 24, 2023].
López-Giménez et al., "Hallucinogens and serotonin 5-HT 2A receptor-mediated signaling pathways", published 2017; https://www.ncbi.nlm.nih.gov/pmc/articles/PMC5756147/pdf/nihms916003.pdf [retrieved Jul. 24, 2023].
Millière et al., "Psychedelics, meditation, and self-consciousness", published Sep. 2018; https://www.ncbi.nlm.nih.gov/pmc/articles/PMC6137697/pdf/fpsyg-09-01475.pdf [retrieved Jul. 24, 2023].
Nichols, David E., "Psychedelics", published Apr. 2016; https://www.ncbi.nlm.nih.gov/pmc/articles/PMC4813425/pdf/pr.115.011478.pdf [retrieved Jul. 24, 2023].
Menon et al., "Combined EEG and fMRI studies of human brain function", published Feb. 2005; https://med.stanford.edu/content/dam/sm/scsnl/documents/Menon_Combined_EEG_05.pdf [retrieved Jul. 24, 2023].
Berkovich-Ohana et al., "Meditation, absorption, transcendent experience, and affect: tying it all together via the consciousness state space (CSS) model", published Jan. 2016; https://www.researchgate.net/publication/289244862_Meditation_Absorption_Transcendent_Experience_and_Affect_Tying_It_All_Together_Via_the_Consciousness_State_Space_CSS_Model [retrieved Aug. 3, 2023].
Faber et al., "EEG microstates during different phases of transcendental meditation practice", published Apr. 2017; https://www.zora.uzh.ch/id/eprint/141957/1/Faber_2017_acceptedManuscript.pdf [retrieved Jul. 24, 2023].
Non-Final Office Action mailed Nov. 8, 2023 for U.S. Appl. No. 18/305,775.
Singh et al. "Towards the development of personalized and generalized interfaces for brain signals across different styles of meditation". Proceedings of the Thirteenth Indian Conference on Computer Vision, Graphics, and Image Processing. Dec. 2022. Article No. 54, pp. 1-9. (Year: 2022).
Notice of Allowance mailed Dec. 15, 2023 for U.S. Appl. No. 18/305,775.
U.S. Appl. No. 18/305,775, filed Apr. 24, 2023.
U.S. Appl. No. 18/341,944, filed Jun. 27, 2023.
Travis et al., "Default mode network activation and Transcendental Meditation practice: Focused Attention or Automatic Self-transcending?", published Feb. 2017; https://www.sciencedirect.com/science/article/abs/pii/S0278262616300987?via%3Dihub [retrieved Aug. 3, 2023].
Travis et al., "Pure Consciousness: Distinct Phenomenological and Physiological Correlates of Consciousness Itself", published Jan. 1999; https://www.researchgate.net/publication/12787032_Pure_consciousness_Distinct_phenomenological_and_physiological_correlates_of_%27consciousness_itself%27 [retrieved Aug. 3, 2023].
Travis, Frederick, "Autonomic and EEG patterns distinguish transcending from other experiences during Transcendental Meditation practice", published Aug. 2001; https://www.sciencedirect.com/science/article/abs/pii/S016787600100143X?via%3Dihub [retrieved Aug. 3, 2023].
Travis, Frederick, "Comparison of coherence, amplitude, and eLORETA patterns during Transcendental Meditation and TM-Sidhi practice", published Sep. 2011; https://www.sciencedirect.com/science/article/abs/pii/S0167876011001851?via%3Dihub [retrieved Aug. 3, 2023].
Travis, Frederick, "Transcendental experiences during meditation practice", published Dec. 2013; https://nyaspubs.onlinelibrary.wiley.com/doi/10.1111/nyas.12316 [retrieved Aug. 3, 2023].
Fingelkurts et al., "EEG-guided meditation: A personalized approach", published Dec. 2015, https://www.bm-science.com/images/bms/publ/art83.pdf [retrieved Aug. 15, 2023].
Non-Final Office Action mailed Feb. 4, 2026 for U.S. Appl. No. 18/341,944.

* cited by examiner

420

| | RULE (450) | METRIC (452) | FREQUENCY BANDS (454) | LOCATION (456) | WEIGHT (458) |
|---|---|---|---|---|---|
| 412 | 1 | POWER | DELTA (1-4) | FRONT | -1 |
| 414 | 2 | %POWER | THETA1 (4-6) | BACK | -1 |
| 416 | 3 | CONNECTIVITY | THETA2 (6-8) | FRONT | 1 |
| 418 | 4 | COMPLEXITY | ALPHA1 (8-10) | FRONT | 2 |

FIG. 4A

420

| | RULE (450) | METRIC (452) | FREQUENCY BANDS (454) | LOCATION (456) | WEIGHT (458) |
|---|---|---|---|---|---|
| 412 | 1 | POWER | DELTA (1-4) | FRONT | 0 |
| 414 | 2 | %POWER | THETA1 (4-6) | BACK | -2 |
| 416 | 3 | CONNECTIVITY | THETA2 (6-8) | FRONT | -2 |
| 418 | 4 | COMPLEXITY | ALPHA1 (8-10) | FRONT | 1 |
| 422 | 5 | POWER | BETA | BACK RIGHT | -2 |
| 424 | 6 | COHERENCE | GAMMA | LEFT | -1 |

FIG. 4B

BRAIN STATE RULE GENERATION AND SCORING SYSTEM AND METHOD

TECHNICAL FIELD

The present disclosure generally relates to methods and systems for developing rules promoting specific brain states, and in particular to methods and systems for providing users with tailored protocols and scoring to facilitate desired changes to their brain's electrical activity.

BACKGROUND

In recent years, there has been significant uptake of meditation and related relaxation techniques as a means of alleviating stress and maintaining good health. Meditation offers a safe, effective, and relatively inexpensive intervention for reducing chronic stress and other stress-related disorders, in addition to improving cognition, mood, sleep, and general well-being. Despite its popularity, little is known about the neural mechanisms by which meditation works, and there remains a need for more rigorous investigations of the underlying neurobiology of individual brain states. Considering the wide range of possible meditation techniques and associated brain states, it may be appreciated that different practices will produce different electrophysiological effects—and that individuals with different neuropsychological profiles will respond differently to each practice style. Indeed, in some respects, individual responses to each practice can affect the suitability of a particular meditation technique for a given individual. A one-size-fits-all approach may not accommodate each person's unique cognitive demands and levels of experience. With the recognition that not every practice style is suitable for everyone, it becomes clear that a more personalized, intelligent approach to promoting brain health is needed.

There is a need in the art for a system and method that addresses the shortcomings discussed above.

SUMMARY

In one aspect, a method for generating rules that target brain states of specific meditation styles is disclosed. The method can include a first step of receiving, at a rule generation system, a first brain activity dataset that includes a set of metrics reflecting assorted EEG data for multiple human persons each practicing one of a plurality of meditation styles, and a second step of classifying, at the rule generation system, each metric of the set of metrics under one meditation style, where a first metric is classified under a first meditation style and the second metric is classified under a second meditation style. In addition, the method can include a third step of generating, at the rule generation system, a first rule targeting a brain state associated with the first meditation style that is based on the first metric, and a fourth step of generating, at the rule generation system, a second rule targeting a brain state associated with the second meditation style that is based on the second metric. The method can also include a fifth step of providing, via a user interface for an application associated with the rule generation system accessed via a first computing device, a first brain activity training session based on the first rule that is configured to promote the first meditation style.

In another aspect, a method for evaluating and scoring brain activity is disclosed. The method includes a first step of receiving, at a depth scoring system, a baseline dataset representing brainwave activity for a first user in an eyes closed condition over a first time period, and a second step of determining, by the depth scoring system and for the baseline dataset, values for a first set of metrics. This method can also include a third step of receiving, at the depth scoring system, a meditation dataset representing brainwave activity for the first user in a meditative condition over a second time period, and a fourth step of segmenting, at the depth scoring system and by regular time intervals, the meditation dataset into multiple subsets that includes a first subset, the first subset corresponding to brainwave activity over a first time interval. In addition, the method can also include a fifth step of determining, by the depth scoring system and for the first subset, values for a second set of metrics, and a sixth step of calculating, at the depth scoring system and for the first subset, a z-score for each metric in the second set of metrics by reference to an average value and/or standard deviation for that metric in the baseline dataset, thereby generating a first set of z-scores characterizing the brainwave activity over the first time interval. Finally, the method can include a seventh step of obtaining a first set of weighted z-scores by applying, to each z-score in the first set of z-scores, a first weight that is selected by the depth scoring system based on a first meditation style selected by the first user for practice during the second time period, and an eighth step of calculating, at the depth scoring system, a first composite weighted average of the first set of weighted z-scores, and generating a first personalized brain activity score for the first time interval based on the first composite weighted average.

In another aspect, a method for generating rules that promote a specific brain state. This method can include a first step of receiving from a first user, at a rule generation system, a first input indicating the first user's perception of their brain state during a data collection session and a second step of receiving, at the rule generation system, a first recording of brainwave data for the first user captured during the data collection session that includes first brainwave data. In addition, the method can include a third step of classifying, at the rule generation system, the first brainwave data under a first brain state based on the first input, and a fourth step of extracting, from the first brainwave data and via the rule generation system, values for a first set of metrics including a first metric that characterize the first brainwave data. Furthermore, the method may include a fifth step of calculating, at the rule generation system, an average z-score for each metric in the first set of metrics, thereby generating a first set of average z-scores, a sixth step of generating, at the rule generation system, a first rule based on the average z-score for the first metric, and a seventh step of implementing a first brain activity training session configured to promote the first brain state that is based on the first rule.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIGS. 4A and 4B present examples of weight assignments for a set of rules generated for a brain state protocol, according to an embodiment;

DESCRIPTION OF EMBODIMENTS

Figure 1A:
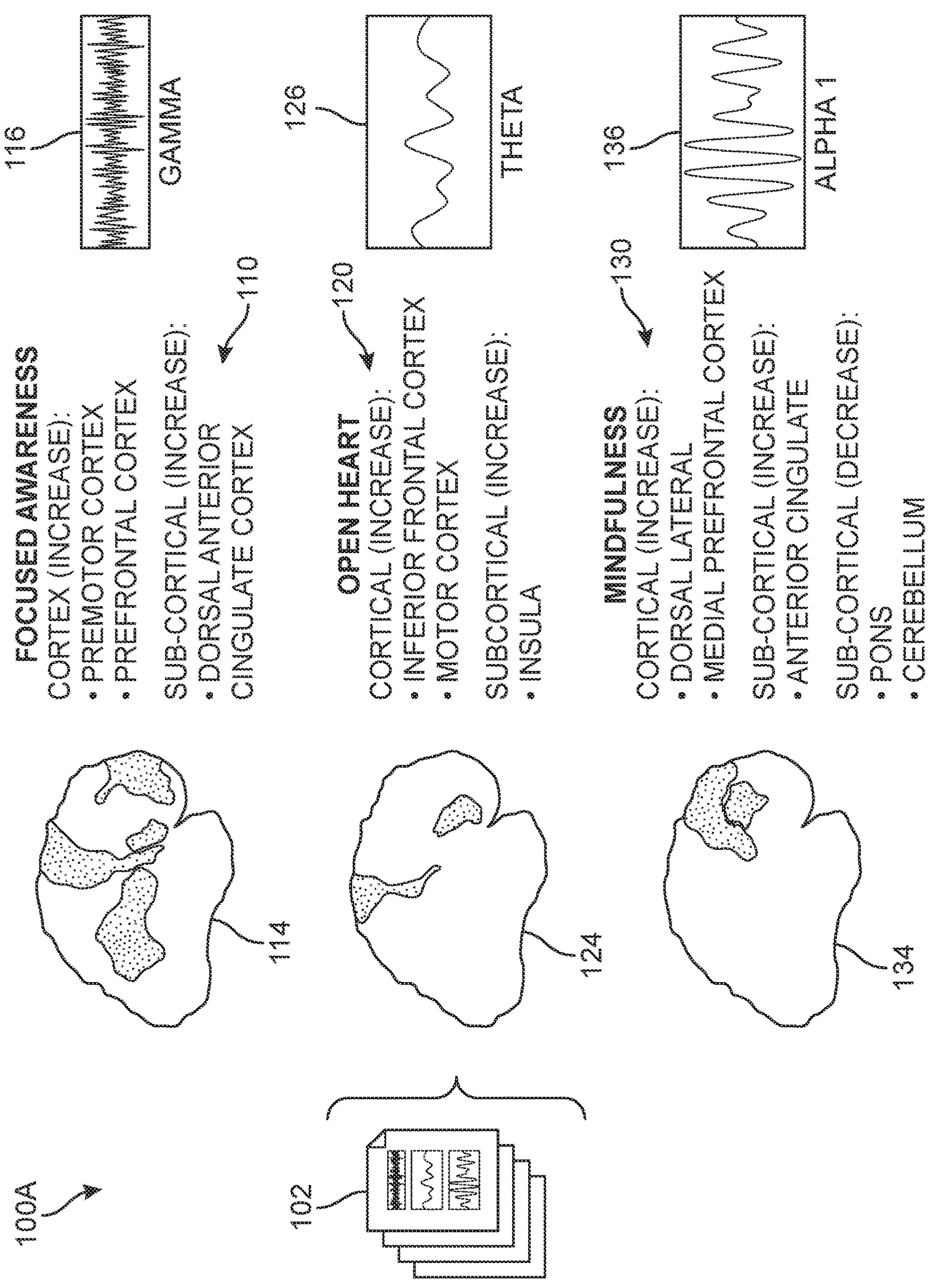
FIGS. 1A and 1B depict an overview of a process of developing protocols for a variety of meditation styles and experience levels, according to an embodiment.

Systems and methods to facilitate and improve EEG-based brain state training are disclosed. In some examples, the embodiments enable a meditation training platform with outcomes far more effective than conventional programs by providing users with mechanisms by which to customize their experience, goals, rewards, and target brain states based on their desired style of practice, level of expertise, and type of brain. The proposed systems allow for significantly more accurate feedback as well as an expedited learning cycle that supports, guides, and intelligently reinforces the brain activity selected by a user. In one example, the system provides a pre-established group of twelve or more carefully crafted, unique protocols, with each protocol including an additional set of sub-protocols that target specific meditation experience levels. In one embodiment, the system provides over 20 protocols, including both traditional meditation-driven protocols and modern results-driven protocols. In yet other embodiments, and as will be described in greater detail further below, the system is configured to create individualized protocols for individuals or groups of individuals, enabling development of an endless variety of custom protocols and implementation options.

As a general matter, EEG or electroencephalography is a method by which spontaneous electrical activity of the brain. Thus, a "brainwave" captured via EEG techniques can refer to a kind of traceable neurophysiological energy in a living brain. These bio-signals detected by EEG have been shown to represent the postsynaptic potentials of pyramidal neurons in the neocortex and allocortex. Voltage fluctuations measured by an EEG bio-amplifier and electrodes allow for monitoring of a person's brain activity. As the electrical activity monitored by EEG originates in neurons in the underlying brain tissue, the recordings made by the electrodes on the surface of the scalp vary in accordance with their orientation and distance to the source of the activity (i.e., brain location). For example, a healthy human EEG will show certain patterns of activity which correlate with how awake a person is. The amplitude of brainwaves is normally measured using microvolt unit (μV). Traditionally, a low amplitudes fall under 20 μV, medium amplitudes between 20-50 μV, and high amplitude are greater than 50 μV. The standard range of frequencies one observes in humans are between 1 to 30 Hz and above, with amplitudes varying between 20 to 100 μV. These observed frequencies have been subdivided in various groups, including: alpha (8-13 Hz), beta (13-30 Hz), delta (0.5-4 Hz), theta (4-7 Hz), and gamma (+30 Hz). Furthermore, the recorded shapes of sinusoidal brainwaves have two main features: up and down, or down and up (i.e., in oscillation). Although the description below will primarily focus on the use of brainwaves captured via EEG, it should be understood that in different embodiments, the proposed embodiments can be implemented based on data obtained via other neuroimaging techniques, including but not limited to ECog, MEG, fMRI, etc.

Furthermore, electrodes—sensor elements that detect the EEG signals and converts them into electrical signals—can be positioned to acquire data from specific brain anatomy locations or areas. These areas can be identified by their relative positions: front, back, left, and right, as well as the cingulate cortex situated in the medial aspect of the cerebral cortex. With these directional identifiers, quadrants (front-left, front-right, back-left, back-right) for the brain areas can be used. An EEG then reflects correlated synaptic activity caused by post-synaptic potentials of cortical neurons. The electric potentials generated by single neurons are far too small to be picked up by an EEG; instead, EEG activity reflects the summation of the synchronous activity of thousands or millions of neurons that have similar spatial orientation, radial to the scalp. As noted above, scalp EEG activity shows oscillations at a variety of frequencies. Several of these oscillations have characteristic frequency ranges and spatial distributions and are associated with different states of brain functioning (e.g., waking and the various sleep stages). These oscillations represent synchronized activity over a network of neurons. The neuronal networks underlying some of these oscillations are understood, while many others are not.

Figure 1B:
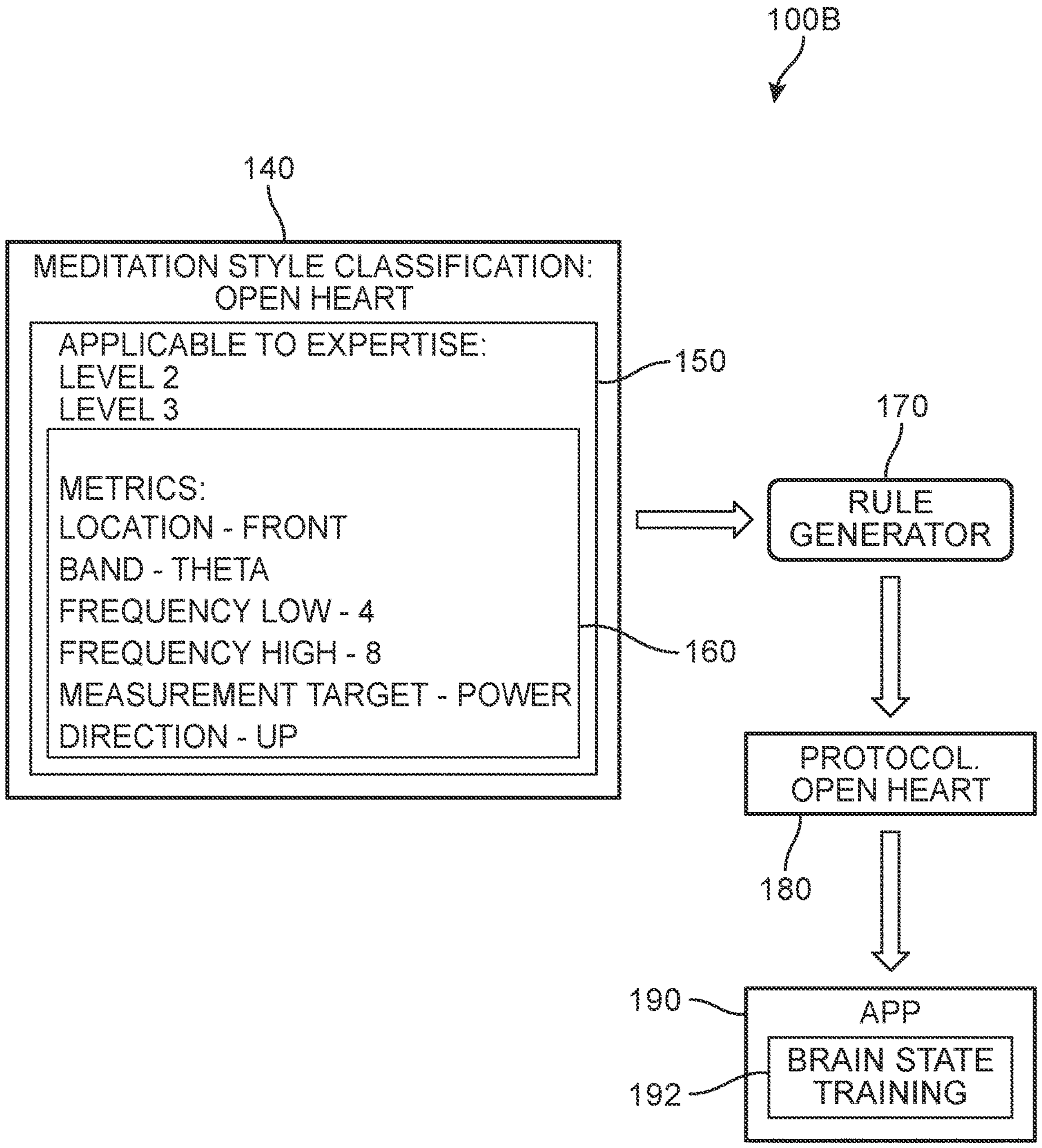

For purposes of introduction, an example of an overview of a protocol development process 100*a* and 100*b* (collectively referred to as process 100) is presented with reference to FIGS. 1A and 1B. In FIG. 1A, input in the form of brain activity data 102 is obtained. For this example, the brain activity data 102 includes descriptive and statistical data for at least three different meditation practice styles (shown here as Focused Awareness 110, Open Heart 120, and Mindfulness 130). In other embodiments, the input can include data for fewer styles, and/or for other, different meditative styles. In some embodiments, as shown in FIG. 1A, the process 100 can initially involve extraction of pertinent metrics and descriptors from the brain activity data 102. Such extraction is represented in FIG. 1A for each of the three brain states: (a) for Focused Awareness 110 there are first location identifiers 112 that indicate which parts of the brain were active during practice of this type of meditation, accompanied by a first brain diagram 114 highlighting the active areas, as well as a first waveform 116 showing the primary bandwidth in which activity was recorded (i.e., gamma waves); (b) for Open Heart 120 there are second location identifiers 122 that indicate which parts of the brain were active during practice of this type of meditation, accompanied by a second brain diagram 124 highlighting the active areas, as well as a second waveform 126 showing the primary bandwidth in which activity was recorded (i.e., theta waves); and (c) for Mindfulness 130 there are third location identifiers 132 that indicate which parts of the brain were active during practice of this type of meditation, accompanied by a third brain diagram 134 highlighting the active areas, as well as a third waveform 136 showing the primary bandwidth in which activity was recorded (i.e., alpha waves). It is to be understood that the data representations depicted in FIG. 1A are shown for purposes of illustration only, and are not intended to characterize actual data used in generating the protocols.

The process 100 continues in FIG. 1B, where it can be understood that the extracted metrics, features, and other aspects of the brain activity data have been categorized and classified based on meditation style 140 (e.g., Open Heart), what expertise level 150 the data is applicable to (e.g., what meditation experience level was the data directed to, such as Level 2 and Level 3), and, for the subset of the data falling under the specific meditation style 140 and expertise level 150, what values were identified measuring specific data points (metrics 160) in the brain activity data.

In different embodiments, each metric identified in metrics 160 (including, for example, brain activity location, bandwidth, low frequency end, high frequency end, measurement category, and oscillation direction, among others) can then be used to automatically generate a rule, via a rule generator 170, for a protocol 180 targeting the selected meditation style. In this case, the protocol 180 includes at least 5-6 rules, each reflecting a metric extracted from the subset of data associated with open heart meditation and participants with Level 2 and/or Level 3 experience. Once the rules are compiled, the protocol 180 can be implemented by an application ("app") 190 for promoting brain state training 192 with a user. For purposes of this application, a protocol refers to an algorithm that defines—using rules—a particular brain state based on values of metrics associated with that brain state. Each rule is used to guide a person toward the selected brain state, for example by reference to the absolute power of each frequency band (Alpha, Beta, etc.), the relative power of each frequency band, brainwave coherence, and brainwave complexity, as well as other metrics or features that have been detected when a person experiences that specific brain state.

Figure 2:
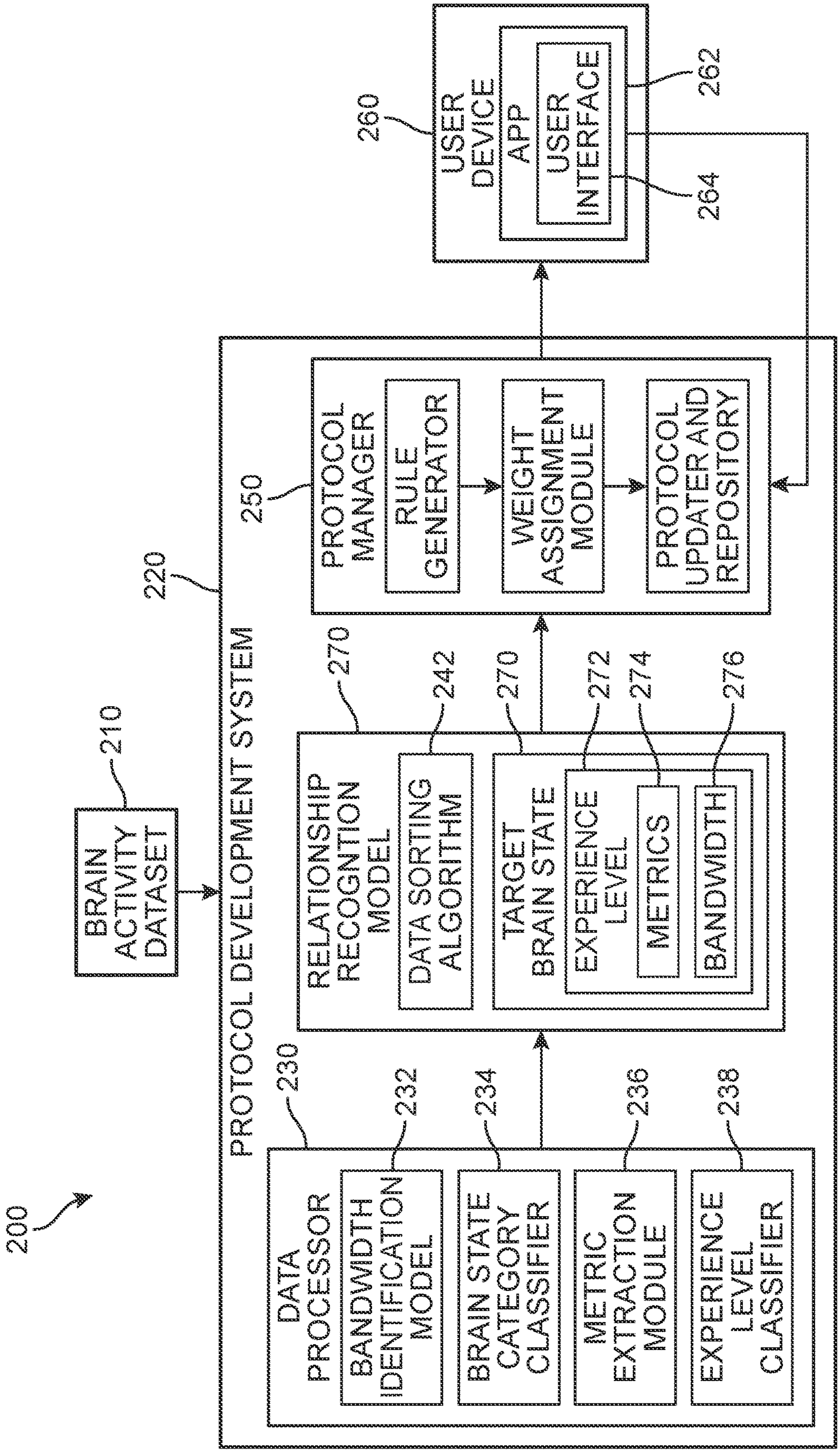
FIG. 2 is a schematic diagram of an environment for implementing a brain state protocol development system, according to an embodiment.

In order to provide the reader with a greater appreciation of the embodiments, FIG. 2 depicts an overview of an embodiment of an environment 200 for implementation of a protocol development system ("system") 220 configured to process, analyze, and extract relevant data points harvested from data collected during research and study of specific meditation practice styles. In some embodiments, the system 220 can also be referred to as a rule generation system. In different embodiments, ongoing batches of state-specific brain activity data ("dataset") 210 can be received by the system 220 at a data processor module 230. Although not depicted in FIG. 2, in different embodiments, the environment 200 can include a client computing device ("client device") configured to communicate with the system 220 over one or more network connections. Thus, in some embodiments, the various components of environment 200 can be accessed through a cloud network and/or stored on a cloud-based server, while in other embodiments some or all components described herein (including some or all modules of system 220) can reside locally in the client device and/or a remote server.

In different embodiments, networks could include one or more Wide Area Networks (WANs), Wi-Fi networks, Bluetooth or other Personal Area Networks, cellular networks, as well as other kinds of networks. It may be appreciated that different devices could communicate using different networks and/or communication protocols. The devices can include computing or smart devices as well as more simple IoT devices configured with a communications module/interface and a sensor. The communication module may include a wireless connection using Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities. In many cases, the communication module is a wireless connection; however, wired connections may also be used. For example, the communication module may include a wired serial bus such as a universal serial bus or a parallel bus, among other connections. In addition, each client device can include provisions for communicating with, and processing information from, system 220. Each device may include one or more processors and memory. Memory may comprise a non-transitory computer readable medium. Instructions stored within memory may be executed by the one or more processors.

Figure 3:
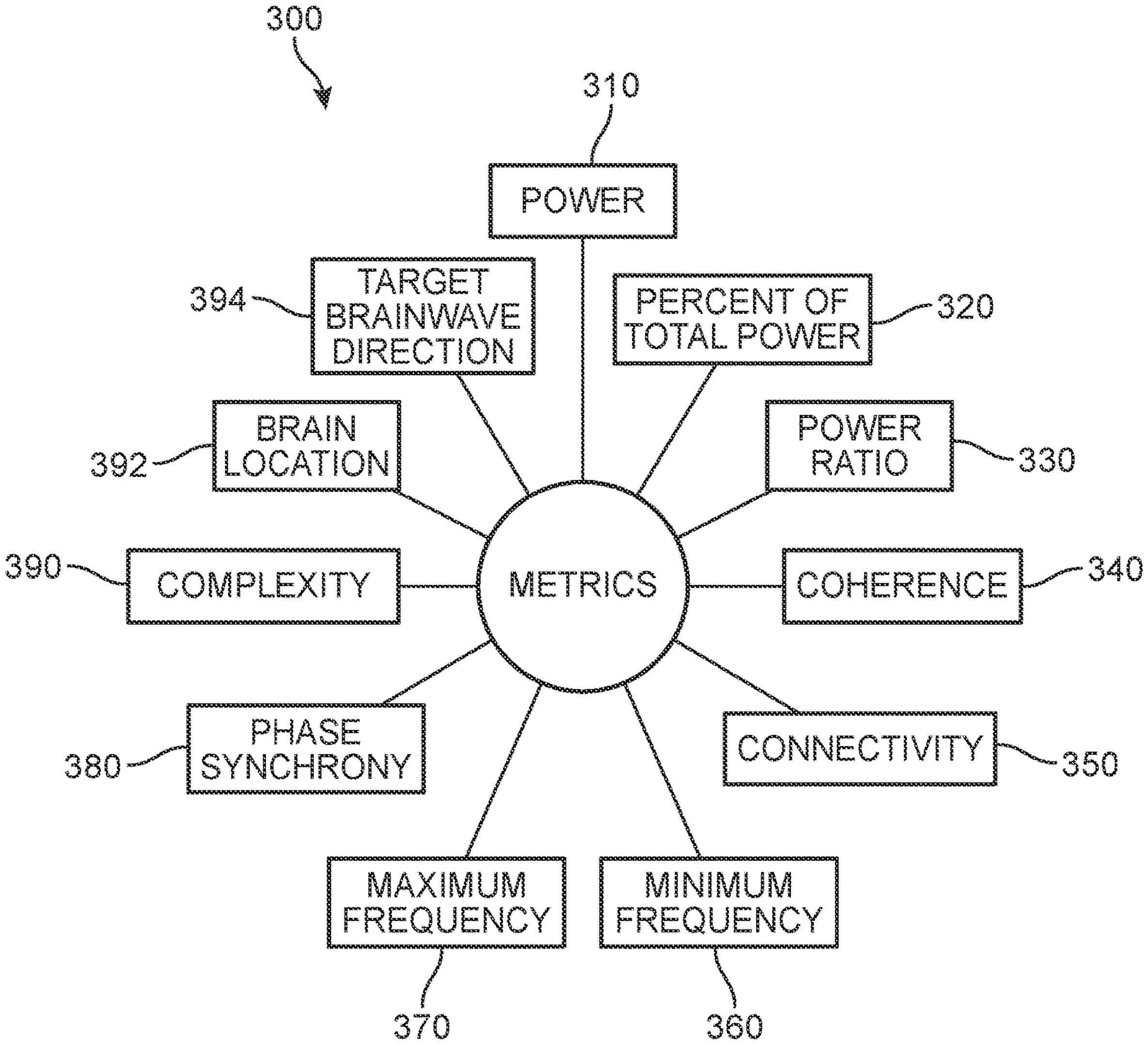
FIG. 3 depicts some examples of metrics that may be used to characterize and describe brain data, according to an embodiment.

In some embodiments, the inputted dataset 210 can represent studies that collected measurements between control groups and meditators where the meditators are put in homogenous groups by technique and experience, and produced results with spectral measurements like amplitude, coherence, synchrony, and complexity (among others) that can be used to score neurofeedback. In other embodiments, the dataset 210 can reflect the EEG data for individuals. In different embodiments, once the dataset 210 is received by data processor module 230, multiple operations may be performed to prepare the data for use by the model. It should be appreciated that the dataset 210 may be unstructured or structured, and include raw data that must initially be processed by one or more filtering and pre-processed. For example, in some embodiments, system 220 is configured to receive each dataset 210 as an input for an intelligent relationship recognition and association machine learning (ML) model ("model") 240. In some embodiments, the dataset 210 is initially segregated or otherwise classified for use by the model 240 to include specific types of information such as but not limited to bandwidth, via a bandwidth identification model 232, brain state category via a brain state category classifier 234, metrics via a metric extraction module 236, and experience level via an experience level classifier 238. In other words, for each dataset 210 received, specific features will be harvested that characterize and structure the data. In one example, the data processor 230 can then generate tagged or labeled data items for ingestion by the model 240. In some embodiments, the labels refer to auto-identifications of the data type—for example, from what specific meditation style was this data created, what expertise did the participants who provided the data have in this meditation style, what bandwidths were primarily activated or present in the data, and a wide range of metrics associated with the data, as will be discussed with reference to FIG. 3.

In one example, bandwidth identification model 232 implements a custom frequency band decomposer that will break any available EEG data into its component frequency bands (e.g., delta, theta, alpha, gamma, beta). In another example, the brain state category classifier 234 can classify each data object as belonging to or representing one or more pre-designated meditation techniques or styles, including Modern Meditations that encompass but are not limited to: (1) Awakened Mind, (2) Calm & Relaxed (3) Creativity, (4) Focus, (5) Mindfulness/Stress Reduction, (6) Open Heart, (7) Quiet Mind. The predesignated style categories can further include Tradition-Based Meditations that include but are not limited to Buddhist Meditations such as (8) Anapana (e.g., mindfulness of breathing), (9) Jhanas (e.g., single-pointed concentration leading to deep states of meditative absorption), (10) Kasina Meditation (e.g., a Samatha-like practice with a focus on kasinas (usually specific shapes, colors, or objects)), (11) Metta (e.g., radiating love and goodwill to ever wider circles of beings), (12) Samatha (e.g., breath/object focus practice for calmness and tranquility), (13) Traditional Mindfulness (e.g., noticing sensations & non-reactivity), (14) Vipassana/Goenka Body-Scanning (e.g., observing sensations in the body to develop tranquility and insight), (15) Vipassana/Thought-Watching (e.g., mindfully observing thoughts without being caught up in them), (16) Zazen/Focused Awareness (e.g., Third Ventricle), (17) Zazen/Open Monitoring (e.g., Shikantaza or "just sitting" to realize your true nature) as well as Vajrayana Meditations including (18) Rigpa (e.g., nondual awareness beyond concepts), (19) Shamatha (e.g., breath/object focus practice for calmness and tranquility), (20) Yidam (e.g., Tantric practice involving visualization of an enlightened being), and Yogic Meditations including (21) Acem Meditation (e.g., transcendental meditation derivative for relaxation and stress management), (22) Brahma Kumaris (BK) Raja Yoga (e.g., thought and visualization-based practices to inhabit soul consciousness), (23) Himalayan Yoga Tradition (e.g., mentally repeating a mantra with breath awareness), (24) Isha Yoga Shoonya (e.g., conscious non-doing to remove emotional and spiritual blocks, (25) Preksha Meditation (e.g., Jain meditation focusing on emotional purification and self-awareness), (26) Satyananda Yoga/Kaya Sthairyam (e.g., body steadiness), and (27) Satyananda Yoga/Japa (e.g., mantra recitation), and also Transcendental Meditations (TM) for transcending mantra recitation to experience blissful unbounded awareness such as (28) TM/Sidhi Practices to develop advanced TM practice (e.g., Samyama). For each of these meditation styles, a different protocol (with different rules and assigned weights) can be crafted based on the associated data objects harvested from the dataset 210, as will be described further below.

In addition, for each of these styles, a different sub-protocol can be generated to reflect the needs of each participant's experience level. As noted above, in different embodiments, the experience level classifier 238 can determine which experience group or level the data is representing, based on pre-designated segmented experience categories, such as: (a) Level 1—Beginner: <10 hours, (b) Level 2—Novice: 10-100 hours, (c) Level 3—Intermediate: 100-1,000 hours, (d) Level 4—Advanced: 1,000-10,000 hours, and (e) Level 5—Expert: >10,000 hours. It should be understood that the ranges in each of these levels are presented as an example, and the category time/hour thresholds can be modified to allow for a more generalized meditation experience by reducing the number of levels, and the hours listed can be in some cases overlapping to accurately represent the fluid nature of meditation expertise and hours of practice for each neuropsychological profile. Furthermore, the protocols can be modified to accommodate individuals who are able to move thorough these stages faster with talent, longer sessions, retreats, and various neurofeedback.

This approach accommodates the understanding that brainwaves (also referred to herein as brain activity) for novice meditators and expert meditators—even for the same meditation style—are very different, and that meditation as a general term encompasses a heterogenous group of practices. For example, meditation techniques could be classified by the area of interest (such as focus on a single object, sound, breath, etc.) or open attention for many objects, or by the cognitive processes such as focused attention or openly monitoring attention, or by the targets, such as concentration on the general mental development or on the growth of primarily specific mental qualities, such as compassion, love, or wisdom.

The ability of the system to develop protocols that take into account the level of experience of the persons providing the data is a vital aspect of the proposed systems. Most conventional meditation studies and their resultant data have been based on participants who were already expert meditators in order to capture brainwaves reflecting distinct altered states of consciousness. If the difference between a student's (beginner or novice) brain and an expert's brain was merely a matter for degree, the experience level might not be as pivotal—the system could be set up with the brain signature of only experts/masters as the "gold standard" and measure the student's depth of meditation by how closely the student's brain wave patterns approximate the brainwave patterns of the masters. However, the process of meditation—or the intentional progression toward any particular brain state—is far more complex in that the patterns of brainwaves that are dominant as the student develops skills and moves to mastery of the technique are not a simple linear progression. Instead, just as there are stages of learning for any complex instrument, students and masters will be engaged on different learning tasks. For example, in learning to play the violin: (a) the beginning violinist is generally focused on note production, and so they have to work hard to produce notes, not squeaks, (b) a novice generally works on tuning and timing (e.g., the C# needs to be a C# and the quarter note needs to be a quarter note), (c) an intermediate violinist may start working on vibrato and tone color, (d) an advanced violinist, who no longer has to think about tuning and time, can start working on expression (e.g., how do the notes flow into each other (or not) and how should the pace and volume go up and down to best express the musical intent), and (e) an expert may hardly think about technique, and instead focus on expressing a musical idea.

Similarly, with this context, the reader may appreciate that a person learning to meditate may also pass through different non-linear stages as they practice a particular technique. For example, a beginner meditator primarily focuses on sitting still and starts to work on quieting the mind, a novice meditator primarily focuses on quieting the mind, an intermediate meditator primarily focuses on honing their skills at maintaining focus, clarity, and equanimity, an advanced meditator has developed their capacity to focus so well that they can focus with ease and so can primarily engage in examining reality with greater detail and clarity (e.g., see the gaps in the perceptions that are usually glossed over), and an expert meditator can use their prodigious focusing skill to dismantle the ego and find oneness. Each of these levels of the same meditation style can thereby be linked to brainwave patterns that are not necessarily “more of the same”. The capacity of the proposed systems to develop protocols that reflect this reality is thus essential to successful meditation practice.

As a non-limiting example, in some contexts, beginner meditators are observed to produce greater alpha, while expert meditators produce very little alpha. In addition, advanced meditators produce more gamma in the back, but not the front, of the brain. Intermediate meditators and advanced meditators produce the most frontal theta, while beginner meditators and expert meditators produce less frontal theta than intermediate meditators. This may be due to theta corresponding to the brainwave of hard-working focus on taming the mind, and intermediate meditators work harder at taming the mind than beginner or expert meditators. These and general tendencies and patterns can be recognized by the system 220 and used to modify protocols developed using data from experts to make them also applicable to advanced, intermediate, novice, and beginning meditators. The system 220 may also recognize these general tendencies and adapt protocols developed for novices and make them applicable to intermediates or above as well. For example, using the tendency described in the above scenario, if the system 220 is adapting a novice meditation protocol to be more suitable for an intermediate meditator, it may automatically reduce the weight assigned to the rule for frontal Alpha and increase the weight assigned to the rule for frontal theta. If the system 220 is adapting an intermediate meditation protocol to be more suitable for a novice meditator, it may automatically increase the weight assigned to the rule for frontal Alpha and reduce the weight assigned to the rule for frontal Theta. As yet another non-limiting example, if the system 220 is adapting an intermediate meditation protocol to be more suitable for an advanced meditator, a rule directed to increasing posterior gamma may be added to the protocol or an existing such rule can have its weight increased, while the weight for the frontal Gamma rule is decreased. On the other hand, if the system 220 is adapting an advanced meditation protocol to be more suitable for an intermediate meditator, weight for the rule for posterior gamma may be reduced, while the weight for the frontal Gamma rule is increased.

In different embodiments, the types or categories of metrics that can be extracted by the metric extraction module 236 can be used to provide a rich, complex representation of a given brain state and experience level. For purposes of reference, some of the metric categories for which data can be captured and used by the system 220 for protocol development are presented in FIG. 3. In some embodiments, metric types 300 can include one or more of power 310, percent of total power 320, power ratio 330, coherence 340, connectivity 350, minimum frequency 360, maximum frequency 370, phase synchrony 380, complexity 390, brain location 392, and target brainwave direction 394. It can be appreciated that these metrics can be representative of a specific bandwidth in the EEG data. In some embodiments, metrics for other brain activity data can be included, such as nuHF, nuLF and LF/HF for ECG. In general, it can be understood that power 310 refers to the microvolts or dB of power in a frequency band, percent of total power 320 (of an EEG) includes the power of a frequency band as a percentage of the total EEG power, power ratio 330 includes ratios such as left/right or theta/beta (or other brain locations or bandwidths), connectivity 350 includes analysis of features such as coherence 340 of the signal, phase lock or phase synchrony 380, etc.), complexity 390 measures the amount of nonlinear/irregular information that a time series conveys over time, brain location 392 includes source localization (e.g., Front, Back, Left, Right, Front Left, Front Right, Back Left, Back Right, Front Back), for example through some form of LORETA, beamforming, or other techniques for functional localization and functional connectivity, and target brainwave direction 394 can be coded as either increasing or decreasing (or up and down) to represent the desired pattern for that meditation style. In some embodiments, bandwidth can be identified as one of alpha, beta, delta, theta, and gamma, and in some cases, sub-bands such as Alpha1 and Alpha2.

In some embodiments, the output of the data processor 230 can then be received by the model 240. A custom data sorting algorithm 242 can then perform a specialized sorting operation each data object can be arranged in a structured data map that explicitly defines the meaning of the data within its relationships. In other words, each metric of metrics 274 and the identified primary bandwidth 276 can be automatically linked to a pre-designated meditation style (targeted brain state 270) and experience level 272. In some embodiments, the sorted data can be arranged as a set of structured data that represents, for each available metric and each detected brainwave bandwidth, a classification catalog that reveals recurring patterns of meditation-related data detected over time and multiple sessions.

Simply for purposes of illustration, one example of a subset of sorted data is shown in Table 1 below. The experience level categories are shown across the top of Table 1 and correspond to the number of hours the participants for whom data was collected in dataset 210 have engaged in the meditation. Table 1 also shows how an individual’s experience can be directly linked to which specific meditation or target brain state protocol is available and can be potentially attainable for them. In addition, it can be appreciated that there may be distinct types of a meditation technique that can only be meaningfully pursued or engaged after a participant has reached a specific experience level.

TABLE 1

| Tradition | Beginner Calming the Body <10 hrs | Novice Calming the Mind & Body~10-100 hrs | Intermediate Effort to maintain Focus, Clarity, & Equanimity~100-1,000 hrs | Advanced More Skill; Less Effort Emptiness of things~1,000-10,000 hrs | Expert Non-dual, Unity, Loss of Self >10,000 hrs |
|---|---|---|---|---|---|
| Relaxation | Relaxation Response | | | | |
| Guided | | Guided Meditation | | | |

TABLE 1-continued

| Tradition | Beginner Calming the Body <10 hrs | Novice Calming the Mind & Body~10-100 hrs | Intermediate Effort to maintain Focus, Clarity, & Equanimity~100-1,000 hrs | Advanced More Skill; Less Effort Emptiness of things~1,000-10,000 hrs | Expert Non-dual, Unity, Loss of Self >10,000 hrs |
|---|---|---|---|---|---|
| Awakened Mind | Deep thought/Insights/Intuition/Creativity/Flow | | | | |
| MBSR/ Mindfulness | Watching Breath (FA) | | | | |
| | | Body Scan/Watching Thoughts (OM) Loving kindness (LK) | | | |
| Focus | | Focus | | | |
| Vedic (Patanjali) | Hatha Yoga | Dharana (Focus) | Dharana/Dhyana (absorption) | | Samadhi |
| Vedic (TM) | | TM | | | Sidhi Training |
| Vedic (ISHA) | Hatha Yoga | Shoonya | | Shoonya/Samyama | Samyama |
| Vedic | Hatha Yoga | Focus on Breath/Candle/Mantra | Jhanas (Absorption)/Mantra | | Adviata |
| Theravadan Buddhism | Anapana/Samatha - Breath following | | | | |
| | | | Vapassana - Body Scan The Four Jhanas | | |
| Tibetan Buddhism | Shamatha-calm abiding with support (Mantra/Visualization) | | | | |
| | | | Vapassana (Focus on the Mind) | | Mahamudra & Dzogchen |
| | | Lojong (Loving Kindness and other five perfections) | | Tibetan Tantra (Deity Yoga) | |
| Zen Buddhism | Breath & Posture focus | | | Zazen/Shkantaza/Koans | |

Thus, the relationship recognition model 240 can be understood to offer intelligently characterized groupings of data linked through two layers (target brain state 270, experience level 272) of classifications. In different embodiments, a protocol manager 250 receives the output from the relationship recognition model 240 and automatically creates, develops, and/or updates the protocols. For example, a rule generator can, for each metric in metrics 274 for a given experience level under a particular meditation style (target brain state 270), generate one rule that will be added to a protocol for that meditation style and experience level via a protocol updater and repository ("repository") 256. A rule will similarly be generated for the bandwidth 276 detected for that experience level under the particular meditation style (target brain state 270). In addition, in some embodiments, each rule can then be assigned a weight via a weight assignment module 254 that calculates the weight that corresponds to the relative importance or significance of that metric (and bandwidth) in successfully producing the target brain state. For example, in different embodiments, a rule weight can be determined initially as a +1 where the data indicates the metric goes up or increases during this brain state, 0 where the data indicates the metric plays no significant role in this brain state, and −1 where the data indicates the metric goes down or decreases during this brain state. If additional data is received that reinforces the direction for a given metric, the weight can be increased or decreased accordingly.

In some embodiments, the various protocols with their associated rules and weights that have been developed can be stored in the repository 256 for access by a user device 260 and implementation by a brain training application ("app") 262. For example, a user may select a specific meditation technique and their current experience level via a user interface 264 presented on their display via the app 262, and in response the app 262 can implement the associated protocol from the repository 256. In some embodiments, the protocols maintained in the repository 256 can also be stored locally on the user device 260 for offline access and updated when re-connected to the system 220.

Furthermore, in different embodiments, a rule that was previously generated for a given protocol may be modified (or updated) as new data is received that can enable a fine-tuning of the meditation experience associated with that protocol. In one embodiment, as feedback 290 is received (e.g., from the users via user interface 264), the protocol manager 250 can adjust weights that were attached to the related rule. In another embodiment, as new data is received with additional research and brain activity dataset inputs, the relationship recognition model 240 can modify its sorting organization for that meditation technique and protocol manager 250 will, in response to such changes, automatically modify the existing protocol, thereby maintaining the most up-to-date and effective implementation for attaining that brain state. Thus, the protocol manager 250 can configured to learn over time. For example, the app 262 may request that the user submit feedback regarding their experience, including whether the proffered protocol was aligned with their intended goals during the current session, or via communications to the user at a later time asking about their experience. Based on the feedback the system can reassess the value of one or more weights and/or rules.

It should be understood that in other implementations, environment 200 can include additional or fewer modules or can include one or more additional computing devices or related server devices. The modules of environment 200 can be associated with the various local computing devices and, for example, can be disposed within the computing device. In alternative implementations, the modules of environment 200 can include independent computing devices that are coupled to, and in data communication with, the local computing devices. As used in this description, the term "module" is intended to include, but is not limited to, one or more computers, processing units, or devices configured to execute one or more software programs that include program code that causes a processing device(s) or unit(s) of the computer to execute one or more functions. Processing units can include one or more processors (e.g., microprocessors or central processing units (CPUs)), graphics processing units (GPUs), application specific integrated circuits (ASICs), or a combination of different processors. In alternative embodiments, systems and modules can each include other computing resources/devices (e.g., cloud-based servers) that provide additional processing options for performing one or more of the machine learning determinations and calculations. The processing units or devices can further include one or more memory units or memory banks. In some implementations, the processing units execute programmed instructions stored in memory to cause system, devices, and modules to perform one or more functions described herein. The memory units/banks can include one or more non-transitory machine-readable storage mediums. The non-transitory machine-readable storage medium can include solid-state memory, magnetic disk, and optical disk, a random-access memory (RAM), a read-only memory (ROM), an erasable programmable read-only memory (e.g., EPROM, EEPROM, or Flash memory), or any other tangible medium capable of storing information.

Moving now to FIGS. 4A and 4B, for purposes of illustration, two tables showing some examples of the protocol development system's outputs are depicted. In FIG. 4A, data for meditators at the Level 2 experience level engaging in the mindfulness technique (style) of meditation have been processed by the relationship recognition model, and the protocol manager has used this data to create a first mindfulness protocol coding table 410. In FIG. 4B, data for meditators at the Level 4 experience level engaging in the mindfulness technique (style) of meditation have been processed by the relationship recognition model, and the protocol manager has used this data to create a second mindfulness protocol coding table 420.

Each of the first mindfulness protocol coding table 410 and second mindfulness protocol coding table 420 are comprised of one or more rules 450 based on the data objects extracted from the inputted datasets. For this set of examples, each rule is based on a metric 452. Each metric 452 is further associated with a dominant frequency band (bandwidth) 454 and a brain location 456. Furthermore, each rule 450 has been assigned a weight 458 based on its system-determined significance in the meditation.

With respect to the Level 2 protocol in FIG. 4A, it can be observed that there is a first rule 412 directed to power with a weight of −1, a second rule 414 directed to percent of power with a weight of −1, a third rule 416 directed to connectivity with a weight of +1, and a fourth rule 418 directed to complexity with a weight of +2. Thus, users who select "Mindfulness" as their desired mediation experience, and indicate an experience level of Level 2, could be automatically provided with brain training that incorporates these four rules and seeks to promote the user's brain activity toward these goals.

The same meditation technique, when approached as a Level 4 meditator, may differ, as reflected in FIG. 4B. It can be observed that while the four rules are still applicable, the weights attached to them have been modified. More specifically, the first rule 412 now has a weight of 0, the second rule 414 now has a weight of −2, the third rule 416 now has a weight of −2, and the fourth rule 418 now has a weight of +1. Furthermore, two additional rules have been generated and added to this protocol, including a fifth rule 422 also directed to power (beta) with a weight of −2, and a sixth rule 424 directed to coherence with a weight of −1.

Figure 5:
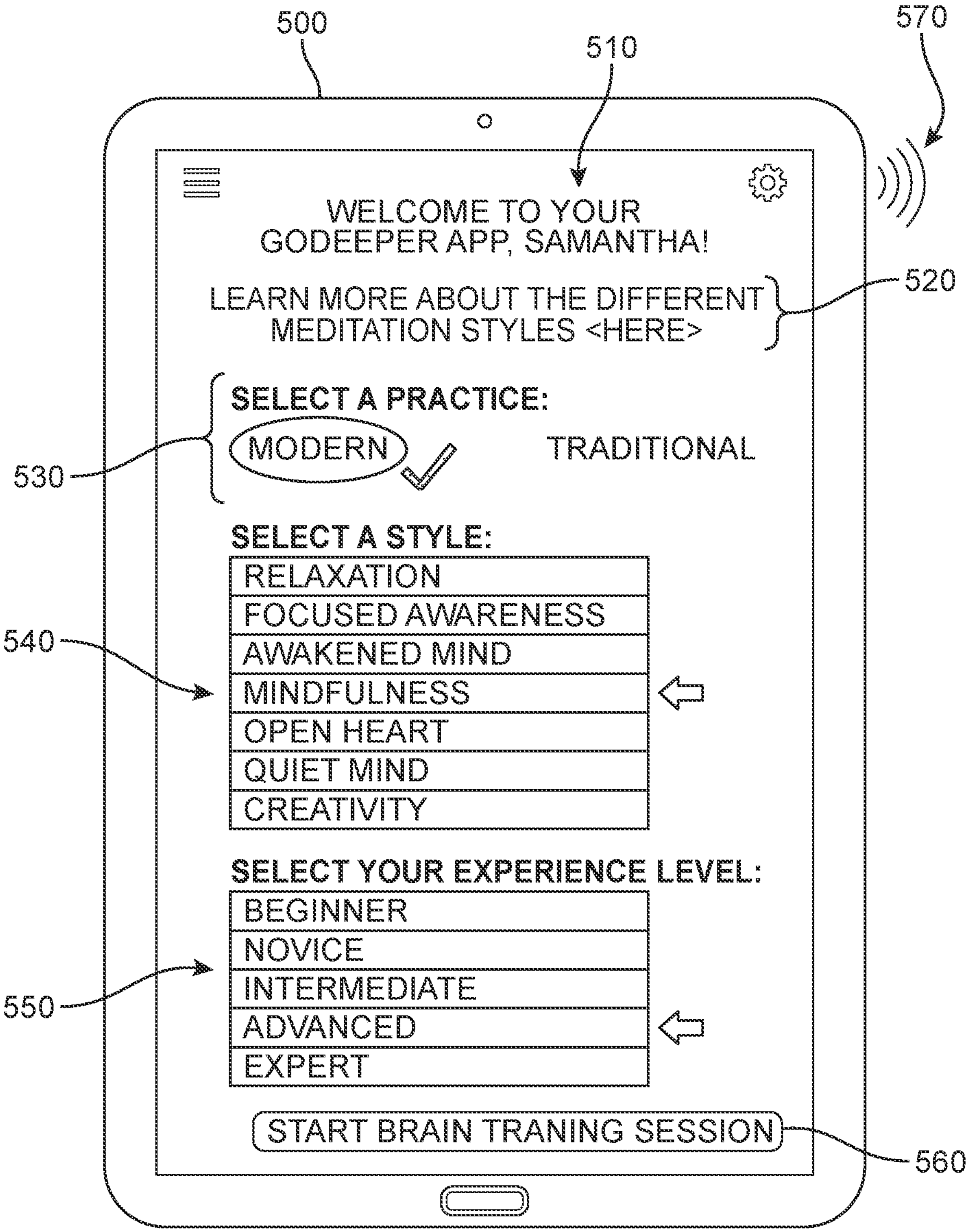
FIG. 5 is one example of a user interface for brain training in which various brain state protocols can be implemented, according to an embodiment.

Referring now to FIG. 5, an example of a user interface for a brain state training application ("app") 510 is presented via a display for a first computing device ("first device") 500. The first device 500 can include an electronics unit comprising a plurality of different components, such as a user interface component (e.g., a touchscreen display, keyboard, mouse, microphone, etc.), a sensor unit (including one or more cameras or other image-based sensors), a user interface module, a processor, and/or a communication module. In some embodiments, the first device 500 may also include a microphone and speaker. In this example, first device 500 is a computer tablet, while in other cases the first device 500 can refer to a mobile device, a smartwatch, a desktop, a laptop, or other computing device. In addition, the first device 500 includes a system including one or more processors and memory. Memory may comprise a non-transitory computer readable medium. Instructions stored within memory may be executed by the one or more processors. The first device 500 may be configured to receive and analyze data from various sensors associated with the sensor unit in the first device 500 or data that is communicated from external components or devices to first device 500. In different examples, the sensor unit includes a variety of sensors. A communication module 570 may allow the first device 500 to communicate wirelessly. In this case, the communication module is illustrated as a wireless connection; however, wired connections may also be used. For example, the communication module may include a wired serial bus such as a universal serial bus or a parallel bus, among other connections. The communication module may also include a wireless connection using Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities In different embodiments, the app 510 can offer a user interface that may be accessed via any user computing device configured for connection to a network. In different embodiments, the application can be configured to offer content via native controls presented via an interface. Throughout this application, an "interface" may be understood to refer to a mechanism for communicating content through a client application to an application user. In some examples, interfaces may include pop-up windows that may be presented to a user via native application user interfaces (UIs), controls, actuatable interfaces, interactive buttons or other objects that may be shown to a user through native application UIs, as well as mechanisms that are native to a particular application for presenting associated content with those native controls. In addition, the terms "actuation" or "actuation event" refers to an event (or specific sequence of events) associated with a particular input or use of an application via an interface, which can trigger a change in the display of the application. This can include selections or other user interactions with the application, such as a selection of an option offered via a native control, or a 'click', toggle, voice command, or other input actions (such as a mouse left-button or right-button click, a touchscreen tap, a selection of data, or other input types).

Furthermore, a "native control" refers to a mechanism for communicating content through a client application to an application user. For example, native controls may include actuatable or selectable options or "buttons" that may be presented to a user via native application UIs, touch-screen access points, menus items, or other objects that may be shown to a user through native application UIs, segments of a larger interface, as well as mechanisms that are native to a particular application for presenting associated content with those native controls. The term "asset" refers to content that may be presented in association with a native control in a native application. As some non-limiting examples, an asset may include text in an actuatable pop-up window, audio associated with the interactive click of a button or other native application object, video or other media associated with a user interface, or other such information presentation. In some embodiments, a user can receive and send information through a user interface that may be presented on the device display. The user interface and display may represent a common component or may represent separate physical or functional components. In some embodiments, the display may be a touchscreen, allowing the customer to interact with the user interface directly by touch. The user interface may refer to an operating system user interface or the interface of one or more software applications that may run on the client device, such as the app.

As shown in FIG. 5, in different embodiments, the app 510 can be configured to offer information 520 and options for brain state training. In a first example, a first option 530 asks the user to select whether they wish to initiate a meditation that falls under the modern practices or the tradition practices. In this case, the user selects the modern practices. In response, the app 510 reveals a plurality of selectable options 540 for meditation styles that fall under the modern practices. In this case, the user selects Mindfulness. In some embodiments, the app 510 can also request that the user select an experience level options 550 that matches their current experience. In some embodiments, the experience level options 550 may also include an option to view additional details about each level, the number of hours associated with the level, and what makes each level distinct from the other levels. In this case, the user selects Level 4. With this information, the app 510 can initiate a brain training paradigm that is tailored to the user's targeted brain state by accessing the unique protocol that was developed by the system for the selected technique at the selected experience level.

Figure 6:
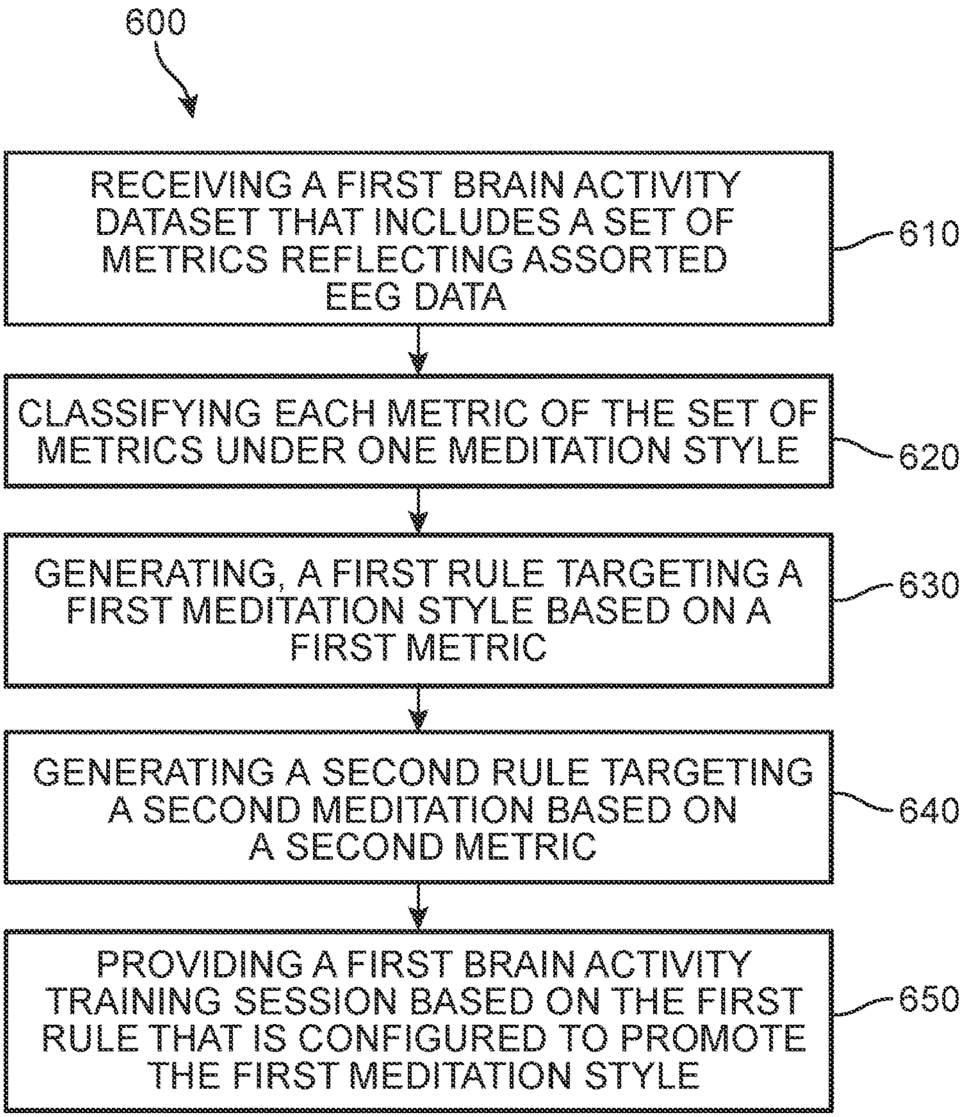
FIG. 6 is a flow chart of a process of intelligent development of protocols that target brain states for specific meditation styles, according to an embodiment.

FIG. 6 is a flow chart illustrating an embodiment of a method 600 for generating rules that target brain states of specific meditation styles. The method can include a first step 610 of receiving, at a rule generation system, a first brain activity dataset that includes a set of metrics reflecting assorted EEG data for multiple human persons each practicing one of a plurality of meditation styles, and a second step 620 of automatically classifying, at the rule generation system, each metric of the set of metrics under one meditation style, where a first metric is classified under a first meditation style and the second metric is classified under a second meditation style. In addition, the method 600 can include a third step 630 of automatically generating, at the rule generation system, a first rule targeting a brain state associated with the first meditation style that is based on the first metric, and a fourth step 640 of automatically generating, at the rule generation system, a second rule targeting a brain state associated with the second meditation style that is based on the second metric. The method 600 can also include a fifth step 650 of automatically providing, via a user interface for an application associated with the rule generation system accessed via a first computing device, a first brain activity training session based on the first rule that is configured to promote the first meditation style.

In other embodiments, this method may include additional steps or aspects. In one example, each metric in the set of metrics represents (e.g., for a given bandwidth) one of power, percent of total power, power ratio, coherence, connectivity, minimum frequency, maximum frequency, phase synchrony, complexity, brain location, and target brainwave direction. In another embodiment, the method also includes creating, via the rule generation system, a first set of rules collectively targeting the first meditation style, and a second set of rules collectively targeting the second meditation style, and presenting, via the user interface, options including a first option to engage in the first meditation style based on the first set of rules and a second option to engage in the second meditation style based on the second set of rules. In another example, the method can include receiving, via the application and at the rule generation system, a user selection of the first option, and selecting, by the rule generation system, the first set of rules based on the user selection of the first option.

In different embodiments, the method can further include steps of receiving, at the rule generation system, a second brain activity dataset that includes a set of metrics reflecting assorted EEG data for multiple human persons each practicing the first meditation style, automatically classifying, at the rule generation system, a third metric extracted from the second brain activity dataset under the first meditation style, automatically generating, at the rule generation system, a third rule targeting the first brain state that is based on the third metric, and automatically updating the first set of rules to also include the third rule. In one example, the first brain activity dataset further includes information about each person's experience level when practicing their meditation style, and the method further comprises automatically classifying, at the rule generation system, each metric of the set of metrics under one of a plurality of experience levels. In some embodiments, the first metric of the set of metrics is further automatically classified under a first experience level for the first meditation style. In such cases the method can also include steps of automatically classifying a third metric of the set of metrics under the first meditation style, automatically classifying the third metric under a second experience level for the first meditation style that is different from the first experience level, and automatically generating, at the rule generation system, a third rule targeting a third brain state associated with the first meditation style for users at the second experience level that is based on the third metric. Furthermore, in one embodiment, the method may also include steps of automatically presenting, via the user interface, options including a first option to engage in a first experience level for the first meditation style and a second option to engage in a second experience level for the first meditation style, and receiving, via the user interface and at the rule generation system, a user selection of the first option, where selection of the first rule rather than the third rule is further based on the user selection of the first option.

In different embodiments, a system for generating rules that target brain states of specific meditation styles is disclosed. The system includes a processor and machine-readable media including instructions which, when executed by the processor, cause the processor to perform some or all of the steps described above.

Other methods may be contemplated within the scope of the present disclosure. In one example, a method for the intelligent development of protocols that target brain states for specific meditation styles is disclosed. The method can include a first step of receiving, at a protocol development system, a first brain activity dataset that can include a set of metrics reflecting assorted EEG data for multiple human persons each practicing one of a plurality of meditation styles. The set of metrics include at least a first metric and a second metric, and each metric in the set of metrics can represent (e.g., for a specific EEG bandwidth) one of power, percent of total power, power ratio, coherence, connectivity, minimum frequency, maximum frequency, phase synchrony, complexity, brain location, and target brainwave direction, among other metric types. A second step can include automatically classifying, at the protocol development system, each metric of the set of metrics under one meditation style. The first metric can be automatically classified under a first meditation style and the second metric can be classified under a second meditation style that differs from the first meditation style. In addition, a third step can include automatically generating, at the protocol development system and for a first protocol targeting a brain state associated with the first meditation style, a first rule based on the first metric, and a fourth step can include automatically generating, at the protocol development system and for a second protocol targeting a brain state associated with the second meditation style, a second rule based on the second metric. The method further can include a fifth step of automatically creating, via the protocol development system, a set of protocols including the first protocol and the second protocol, and a sixth step of automatically presenting, via a user interface for an application associated with the protocol development system accessed via a first computing device, options including a first option to engage in the first meditation style and a second option to engage in the second meditation style. A seventh step can include receiving, via the application and at the protocol development system, a user selection of the first option, an eighth step can include automatically selecting, by the protocol development system, the first protocol from the set of protocols based on the user selection of the first option, and a ninth step can include automatically providing, via the application, a first brain activity training session based on the first protocol that is configured to promote the first meditation style.

In other embodiments, this method may include additional steps or aspects. In one example, the first brain activity dataset further includes information about each person's experience level when practicing their meditation style. In some embodiments, the method also includes automatically classifying, at the protocol development system, each metric of the set of metrics under one of a plurality of experience levels. In some embodiments, each experience level of the plurality of experience level is characterized by the average number of hours needed for a person to attain that experience level for a particular meditation style. In another embodiment, the first metric of the set of metrics is further automatically classified under a first experience level for the first meditation style, such that the first protocol targets a brain state associated with the first meditation style at the first experience level. In such cases, the method can also include steps of automatically classifying a third metric of the set of metrics under the first meditation style, automatically classifying the third metric under a second experience level for the first meditation style that is different from the first experience level, and automatically generating, at the protocol development system and for a third protocol targeting a brain state associated with the first meditation style at the second experience level, a third rule based on the third metric.

In different embodiments, the method can also include steps of automatically presenting, via the user interface, options including a third option to engage in a first experience level for the first meditation style and a fourth option to engage in a second experience level for the first meditation style, and receiving, via the user interface and at the protocol development system, a user selection of the third option, where selection of the first protocol by the protocol development system is further based on the user selection of the third option. In some embodiments, the method can include receiving, at the protocol development system, a second brain activity dataset that includes a set of metrics reflecting assorted EEG data for multiple human persons each practicing one of a plurality of meditation styles and differs from the first brain activity dataset, and then automatically updating the first protocol in response to the second brain activity dataset including metrics for multiple human persons practicing the first meditation style. In some examples, the update can involve the generation of a new rule based on a different value for a metric identified in the second brain activity dataset. In another example, the update can involve the automatic modification of a previously generated rule based on a different value for a metric identified in the second brain activity dataset affecting the overall outcome. In still another example, the update can involve the automatic creation of another protocol for the same meditation style but targeting a different experience level. In still other examples, the update can include automatic deletion of a previously generated rule that has been shown to be ineffective based on information in the second brain activity dataset. In some embodiments, feedback received from the users of the brain training sessions can also be used to automatically improve the protocols and adjust weights. In some embodiments, the method 600 can include automatically classifying a third metric of the set of metrics under the first meditation style, generating, at the protocol development system and for the first protocol, a third rule based on the third metric, and updating the first protocol to also include the third rule.

In another embodiment, a system for the intelligent development of protocols that target brain states for specific meditation styles is disclosed. The system includes a processor and machine-readable media including instructions which, when executed by the processor, cause the processor to perform some or all of the steps described above.

As a general matter, it should be appreciated that a target brain state may be more effectively and efficiently achieved when feedback is also more accurate. In other words, when a person is seeking a specific brain state they can more readily pinpoint the appropriate 'zone' of brain activity when they receive timely and easy-to-comprehend feedback about their performance, and that feedback is based on a set of parameters (e.g., protocol) that have been selected for facilitating that specified brain state at the person's experience level. As will be described below, a reliable and accurate scoring paradigm can allow each user to react and modify their practice in real-time, significantly improving their practice. Furthermore, in some embodiments, the ability to monitor their meditation depth via a dynamic depth score that is fine-tuned based on the selected protocol and experience level can fundamentally shift how a person approaches their meditation practice.

Figure 7:
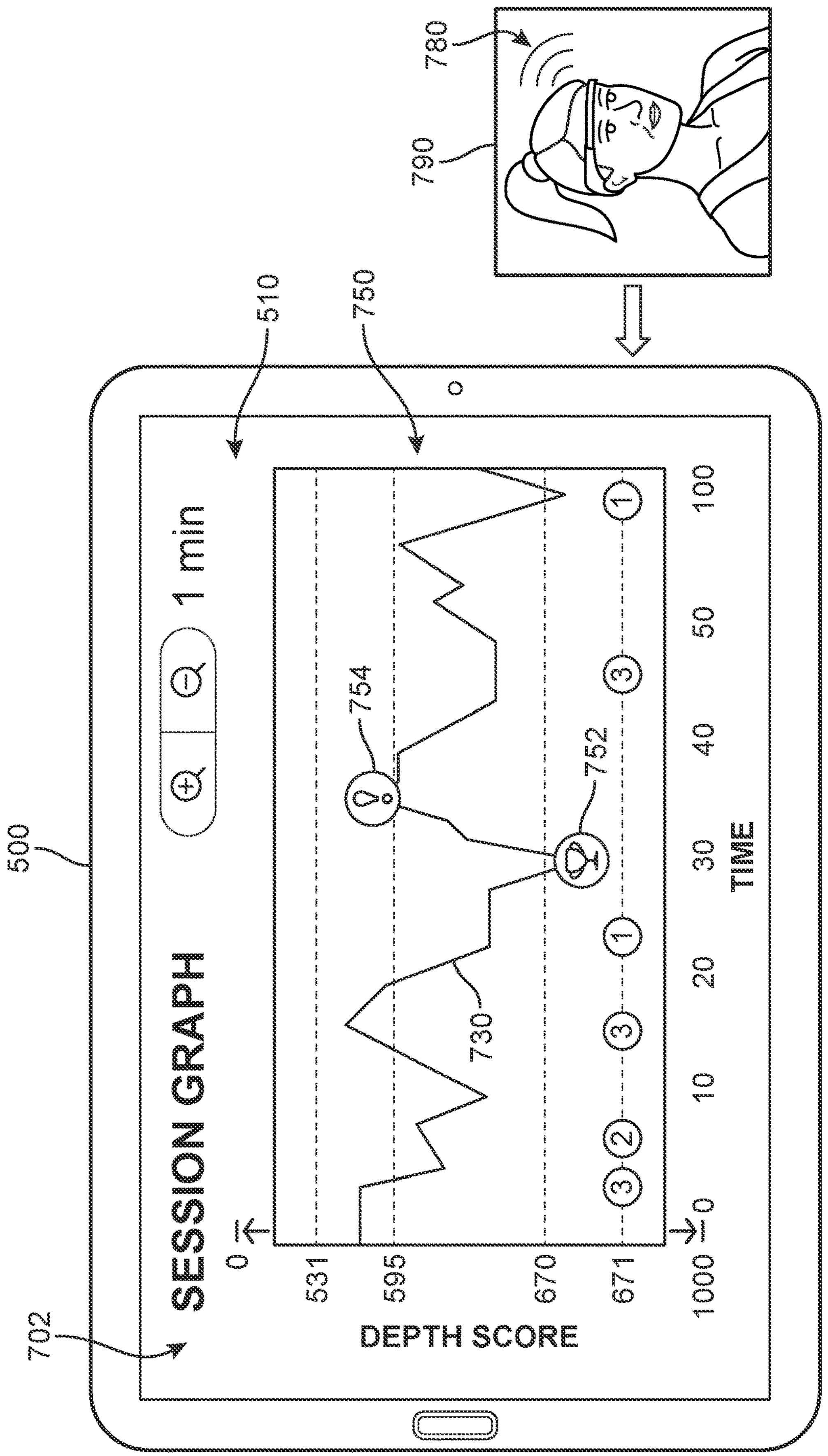
FIG. 7 depicts an example of a user interface in which brain activity scores can be presented that accommodate a variety of meditation styles and experience levels, according to an embodiment.

For purposes of introduction to an embodiment of a brain state depth scoring system, an example of a depth scoring user feedback interface ("depth scoring UI") 702 is shown in FIG. 7. In this example, a real-time or near-real-time depth score visual record 750 is depicted reflecting a meditation session 790 for a user. Brainwave data is collected by an EEG headset and transmitted over a network 780 to the first device 500. The visual record 750 can refer to a graphic or pictorial translation and/or digest of the user's ongoing depth scores during their brain state practice session. The visual record 750 is based on the system's continuous analysis of the user's brain activity as it is received by the first device 500, including the calculation and generation of a sequence of depth scores, a process that will be discussed with reference to FIGS. 8-11 below. As a user engages in their chosen meditation practice, they can be privy to a wide range of feedback, including the visual record 750, that reflect the user's depth score as determined by the system for the milliseconds to seconds immediately preceding the feedback.

More specifically, in the example of FIG. 7, the visual record 750 is a live or near-live time-series graph, with the depth score shown along the Y-axis, and time shown on the X-axis. A first line 730 corresponds to a representation of the magnitude (data points) of the depth scores determined for that time or time increment. In some embodiments, the range of depth scores can be visually sub-divided to offer additional insights such as the depiction of multiple zones indicating the relative depth of the user's brain activity for the selected brain state protocol. Thus, simply for purposes of this example, it can be seen that depth scores less than 595 fall into an undesirable zone, or a zone that is directed away from the target brain state (e.g., wandering mind), while depth scores greater than 670 fall into a desirable zone, or a zone that is moving toward, reinforces, or lies within the target brain state (e.g., meditating mind). In some embodiments, an intermediate zone can also be shown to help the user identify transitional state changes.

Furthermore, in some embodiments, depth scores that enter the desirable zone can be associated with a visual reward 752 (e.g., a trophy, smiley face, checkmark, cute animal, green colored indicator, thumbs-down, or other user-designated icon, etc.) that can encourage or reinforce the user's brain activity and/or a visual warning 754 (e.g., an exclamation mark, sad/confused face, red colored indicator, thumbs down, or other user-designated icon, etc.) that can remind the user to maintain their practice, or help the user catch themselves as they stray from their target. Similarly, other depth score-based feedback can be automatically generated by the app 510, such as audio rewards (e.g., birds chirping, pleasant or gentle music, cheers, or other user-designated sounds, etc.) and audio warnings (e.g., louder or more jarring music, beeps, or other user-designated sounds, etc.), and/or vibration/haptic rewards and warnings (e.g., a first vibration pattern for positive feedback that may be gentle, a second vibration pattern for negative feedback that may be more forceful, etc.).

Figure 8A:
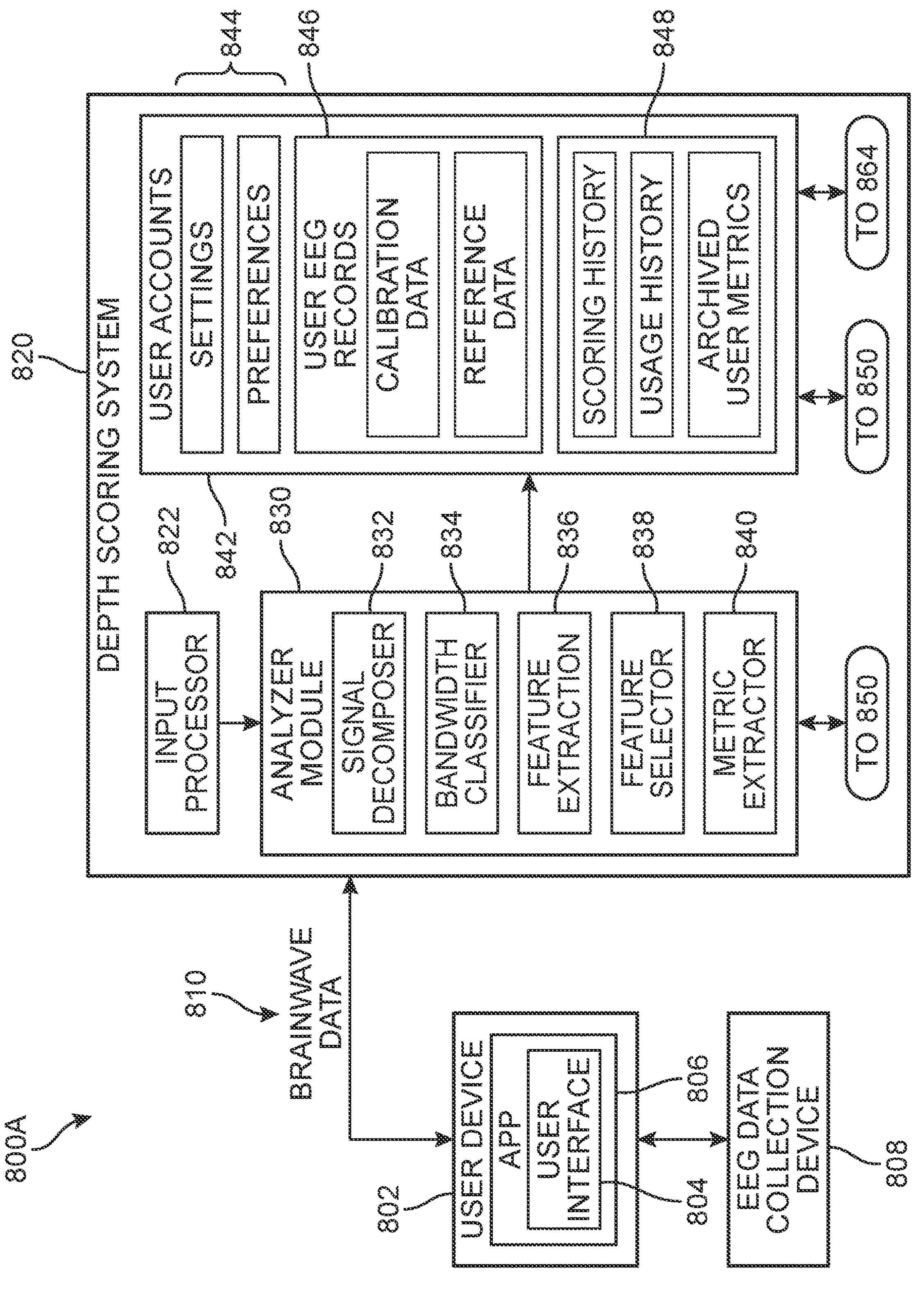
FIGS. 8A and 8B are a schematic diagram of an environment for implementing a brain state depth scoring system, according to an embodiment.
Figure 8B:
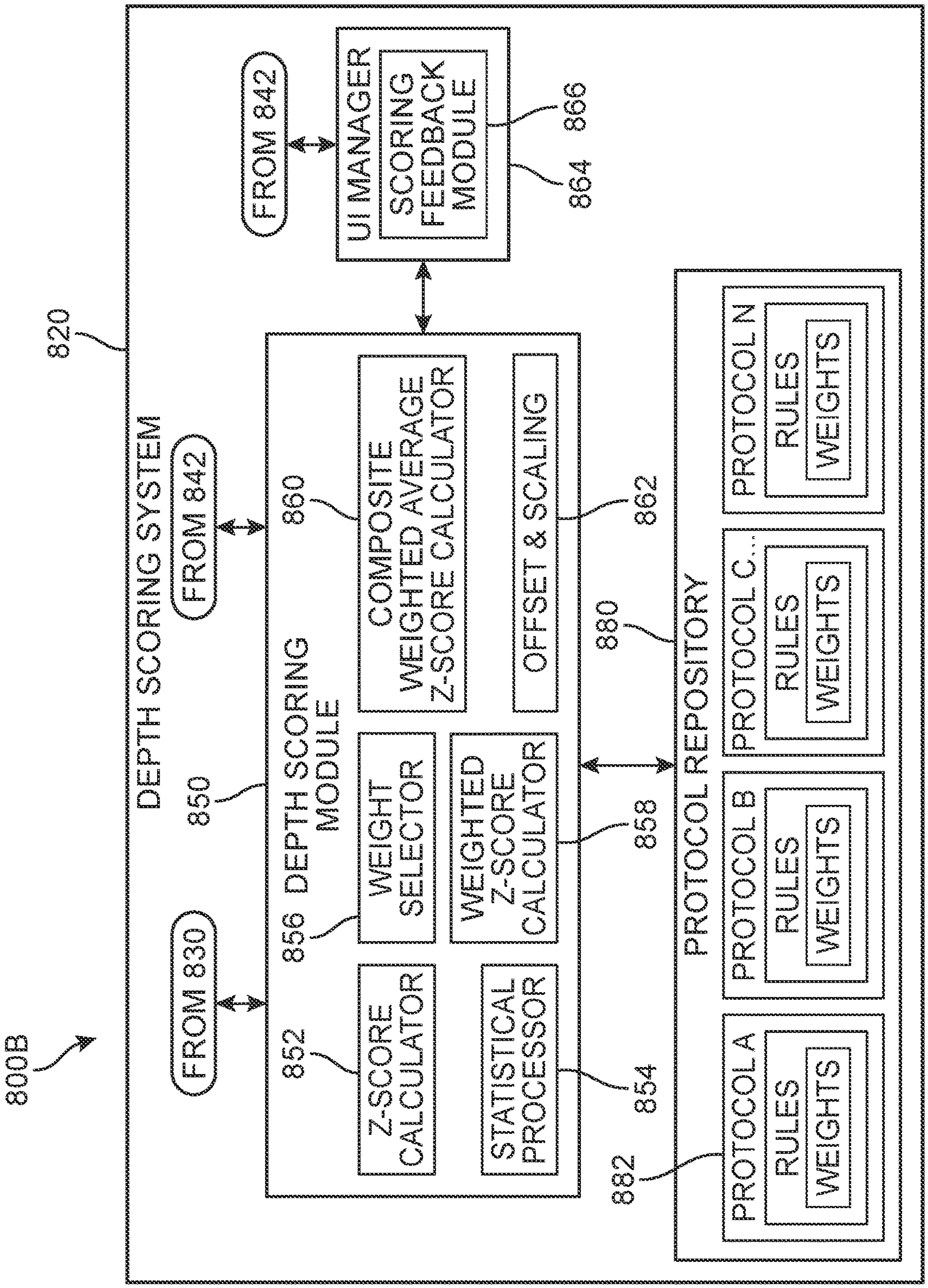

In order to provide the reader with a greater appreciation of the embodiments, FIGS. 8A and 8B depicts an overview of an embodiment of an environment 800 for implementation of a depth scoring system ("system") 820 configured to provide a tailored scoring experience for each of the different styles of meditations at each of the levels of expertise, as described herein.

In contrast, the proposed embodiments are configured to receive EEG data and, across a wide spectrum of brain state goals and experience, identify the appropriate depth score. For example, in different embodiments, a user interface 806 for a depth scoring application ("app") 804 running on a user computing device ("user device") 802 can be in communication with an EEG or other brain-activity collection device 808 via a wired or wireless connection. In different embodiments, the user device 802 and other collection device 808 can also be configured to communicate with the system 820 over one or more network connections. Thus, in some embodiments, the various components of environment 800 can be accessed through a cloud network and/or stored on a cloud-based server, while in other embodiments some or all components described herein (including some or all modules of system 820) can reside locally in the user device and/or a remote server.

In different embodiments, networks could include one or more Wide Area Networks (WANs), Wi-Fi networks, Bluetooth or other Personal Area Networks, cellular networks, as well as other kinds of networks. It may be appreciated that different devices could communicate using different networks and/or communication protocols. The devices can include computing or smart devices as well as more simple IoT devices configured with a communications module/interface and a sensor. The communication module may include a wireless connection using Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities. In many cases, the communication module is a wireless connection; however, wired connections may also be used. For example, the communication module may include a wired serial bus such as a universal serial bus or a parallel bus, among other connections. In addition, each client device can include provisions for communicating with, and processing information from, system 820. Each device may include one or more processors and memory. Memory may comprise a non-transitory computer readable medium. Instructions stored within memory may be executed by the one or more processors.

Thus, in different embodiments, brainwave data 810 such as EEG data obtained via collection device 808 from the user during a brain activity training session (e.g., a person's meditation session or attempt thereof) can be received by system 820, whether the system 820 resides locally whether locally at the user device 802 or remotely over a network connection. In one example, an input processor 822 can receive the brainwave data 810 and prepare the data for use by the system 820. It should be appreciated that the brainwave data 810 can represent raw brain data such as EEG data, which is a complex waveform that includes brainwaves as well as artifacts such as electrical activity of nearby muscles, electrode motion interference, and/or ambient noise. Thus, in some embodiments, input processor 822 can be configured to ensure the data is filtered and pre-processed, and/or made ready for further analysis by downsampling, bandpass filtering, epoch of the data and removal of noisy epochs, removal of noisy components, general artifact rejection/suppression, etc. For example, in one embodiment, a proposed pre-processing pipeline can include several general stages, including filtering, an adaptive technique for artifact removal, interpolation, and independent component analysis (ICA) to remove the artifactual components.

The pre-processed brainwave data 810 is then received by an analyzer module 830. In some embodiments, a signal decomposer module 832 can perform extraction and separation of signal components from the composite signals and further clean the data for use by the other modules of the system 820. In addition, the clean brainwave data 810 can be initially segregated or otherwise classified for use by a bandwidth classification model 834 to determine specific types of information such as but not limited to bandwidth/frequency domain. In some embodiments, a feature extraction operation can initially be performed by a feature extraction module ("feature extractor") 836.

For example, feature extraction can be performed using power spectral density (PSD) and/or log energy entropy. As a general matter, PSD represents the power distribution into the frequency component of the signal, and the latter describes the amount of information carried by a signal or how much randomness is in the signal. In one example, EEG signals can be transformed into PSD using the Fast Fourier Transform and one-second (or other time increment) hamming windows with sufficient overlap to maintain both temporal and frequency resolution and also to minimize the data loss in the window boundary. In addition, in some embodiments, the bandwidth classifier 834 can then divide each EEG channel into a plurality of sub-bands based on its frequency range (e.g., Delta, Theta, Alpha, Gamma, and Beta). As noted earlier, each EEG sub-band has a different frequency range, such that the average power spectrum for each sub-band can be calculated and used for further analysis. In some embodiments, for each sub-band, the average power spectral density ratios may also be calculated. As a non-limiting example, the average PSD of the beta band of each electrode in the frontal area can be divided by the alpha band of each electrode into parietal and occipital regions (frontal beta/parietal occipital alpha), beta divided by theta for each EEG electrode (beta/theta), and theta then divided by (alpha+beta) for each EEG electrode theta/(alpha+beta), and so forth for each of the other PSDs across the different sub-bands and locations.

It can be appreciated that feature extraction from PSD and/or log energy entropy of the EEG sub-bands can generate a large number of extracted features. In such instances, data complexity including the data variance can negatively impact the performance and accuracy of the system 820. Thus, in some optional embodiments, a feature selection module ("feature selector") 838 can be included to reduce dimensionality, improve the predictive accuracy, and enhance the comprehensibility and usability of the obtained results. As some non-limiting examples, feature selector 830 can employ one or more feature selection algorithms, such as recursive feature elimination (RFE) and Lasso cross-validation (LassoCV) among others, to choose the most pertinent subset of the original features by automated removal of the irrelevant or redundant features.

In different embodiments, a metric extraction module ("metric extractor") 840 can calculate and produce a plurality of metrics that can be used by a depth scoring module 850 to evaluate the user's recorded brain activity. Some examples of the metrics that can be identified were described above with reference to FIG. 3. Thus, in different embodiments, the metric extractor 840 enables the system 820 to organize the analyzed data and store values for brain-related metrics including, for each sub-band, power, percent of total power, power ratio, coherence, connectivity, minimum frequency, maximum frequency, phase synchrony, complexity, brain location, and target brainwave direction. In some embodiments, the analyzer module 830 generates values for data points across pre-specified equal time increments. Thus, the EEG data can be pre-segmented into multiple, equal time increments by the analyzer module 830 and, for each time increment of the multiple increments, identify the values of a plurality of metrics. In one example, the metrics are captured for each second, using a second-by-second segmentation of the data, though in other embodiments, the time increment selected can vary from less than a second to 10 or more seconds.

In different embodiments, the system 820 includes or is configured to access one or more databases, such as a user accounts database 842. The user accounts database 842 can include a content library that stores account data related to one or more users. The data may include, for each user, a username, a user profile, user selected settings and preferences 844 such as feedback thresholds, feedback type designations, brain training audio, language, subscription level, etc. Furthermore, each user account may further include a user EEG record repository 846 that stores previous EEG data, raw and/or processed and associated data (e.g., metrics). For example, in different embodiments, the system 802 can request and/or receive multiple brainwave data records. For example, in some embodiments, a user can submit at least a first set of brainwave data corresponding to a reference or baseline ("reference data") and a second set of brainwave data corresponding to a calibration or brain activity recorded during engagement by the user with an active meditation or brain training session. As a general matter, the reference data can refer to EEG data that is collected while the user is in an "eyes closed" or "rest" condition (reference session), and the calibration data can refer to EEG data that is collected during the user's selected meditation style and level of experience (training session or calibration session). Additional data for each user, such as their past scores (scoring history), app usage history, and archived user metrics (user historical data 848) can also be optionally stored in or accessed by user accounts database 842. In some embodiments, this information can be retrieved by a UI manager 864 in response to user requests for account data and/or a description of their past performance and efforts across different mediation styles/levels. In other words, the UI manager 864 can present a summary of the user's brain training sessions as filtered by the meditation (brain state) protocol that was selected, as well as the selected level of experience that was indicated.

In different embodiments, the analyzer module 830 can perform its various operations on multiple sets of brainwave data that are received for a user. For example, the analyzer module 830 can process both the reference data and the calibration data and generate two sets of outputs. In some embodiments, the depth scoring module 850 can receive these outputs of the analyzer module 830, which can be used in turn to perform a specific sequence of operations that enable the brainwave data to be scored and assessed for its adherence to the selected protocol (depth) based on composite data.

In one example, the user can be requested to provide a few to several minutes of reference data and two minutes of meditation type-specific and experience level-specific calibration/practice data. In other embodiments, the amount of time over which data is collected can vary based on the user's preferences, including shorter durations (e.g., one minute) and longer durations (200 seconds, 3 minutes, 5 minutes, 10 minutes, and 20 or more minutes).

As will be described in greater detail below, in different embodiments, the data harvested from the calibration session can be used to calculate depth scores for neurofeedback on a 1-1000 scale, by reference to the baseline data. In one embodiment, for each rule of the selected protocol (e.g., see FIGS. 1B and 2), a Z-score calculation module ("Z-score calculator") 852 can calculate the Z-score for a pre-selected time increment in the calibration session by a formula where each Z-score=reading (value) for a specific metric during the calibration session over the time increment—the average for that metric across the reference session. As noted earlier, in one example, the metrics can reflect one second of data.

Thus, for two minutes of data analyzed, there would be 120 time increments, and an associated 120 metric sets (one set of metrics for each second of EEG data).

In some embodiments, a statistical processor 854 can determine, for each metric, a standard deviation (SD) for the calibration data based on the reference data. In one optional embodiment, the depth scoring module 850 can establish a score range to improve score accuracy, including a minimum score (e.g., at −3 SDs) and a maximum score (e.g., at +3 SDs). A weight selection module 856 can then access weights for the rule linked to the given metric by reference to a protocol repository 880, which can store each of the available protocols 882, including each protocol's rules and each rule's assigned weight, as described earlier. The weight selection module 856 identifies the protocol that was used by the user during the calibration session, determines which rule matches the metric being used, and access the appropriate weight for use by a weight Z-score calculation module ("Z-score calculator") 858. In other words, in some embodiments, each Z-score that is calculated for a given metric can be adjusted based on the rule weight associated to that metric (for the protocol that was chosen for training by the user). Thus, for each Z-score, a weighted Z-score is calculated by multiplication of the Z-score by the weight. In a next operation, a composite weighted average Z-score calculation module ("composite weighted average Z-score calculator") 860 receives the weighted Z-scores and calculates the composite average for all of the metrics for each time increment. In some embodiments, an optional offset can be applied to each of the composite weighted average Z-scores by an offset and scaling module 862. In one example, the value of a first offset can be selected to bring the lowest of the composite weighted average Z-scores to zero, and the value of a second offset can be selected to bring the highest of the composite weighted average Z-scores to the desired maximum. In addition, in some embodiments, a scaling multiplier may be applied to allow for a clearer distribution of scores, on a scale that is readily interpretable by humans. For example, each of the composite weighted average Z-scores can be multiplied by a scaling multiplier such as 1000/(maximum composite z-score-minimum composite z-score) (e.g., for a depth score range of 1-1000). In other embodiments, the scaling multiplier can be greater or smaller depending on the scoring range desired for user feedback.

In different embodiments, these composite weighted average Z-scores can then be used to score the user's brain activity during their selected meditation style and experience level. The scores can then be shared with UI manager 864 for digestion and representation via scoring feedback module 866, which may for example depict the scores in a time-series graph. In some embodiments, the scoring process can be performed by the system 820 in real- or near-real-time as the calibration data is being received. In other embodiments, the process can be performed after the calibration data is received. In one embodiment, the process is performed locally on the user's device via app 804. In another embodiment, some or all operations of the process are performed remotely and results are returned to the user's device over a network connection.

It should be understood that in other implementations, environment 800 can include additional or fewer modules or can include one or more additional computing devices or related server devices. The modules of environment 800 can be associated with the various local computing devices and, for example, can be disposed within the computing device. In alternative implementations, the modules of environment 800 can include independent computing devices that are coupled to, and in data communication with, the local computing devices. As used in this description, the term "module" is intended to include, but is not limited to, one or more computers, processing units, or devices configured to execute one or more software programs that include program code that causes a processing device(s) or unit(s) of the computer to execute one or more functions. Processing units can include one or more processors (e.g., microprocessors or central processing units (CPUs)), graphics processing units (GPUs), application specific integrated circuits (ASICs), or a combination of different processors. In alternative embodiments, systems and modules can each include other computing resources/devices (e.g., cloud-based servers) that provide additional processing options for performing one or more of the machine learning determinations and calculations. The processing units or devices can further include one or more memory units or memory banks. In some implementations, the processing units execute programmed instructions stored in memory to cause system, devices, and modules to perform one or more functions described herein. The memory units/banks can include one or more non-transitory machine-readable storage mediums. The non-transitory machine-readable storage medium can include solid-state memory, magnetic disk, and optical disk, a random-access memory (RAM), a read-only memory (ROM), an erasable programmable read-only memory (e.g., EPROM, EEPROM, or Flash memory), or any other tangible medium capable of storing information.

Figure 9:
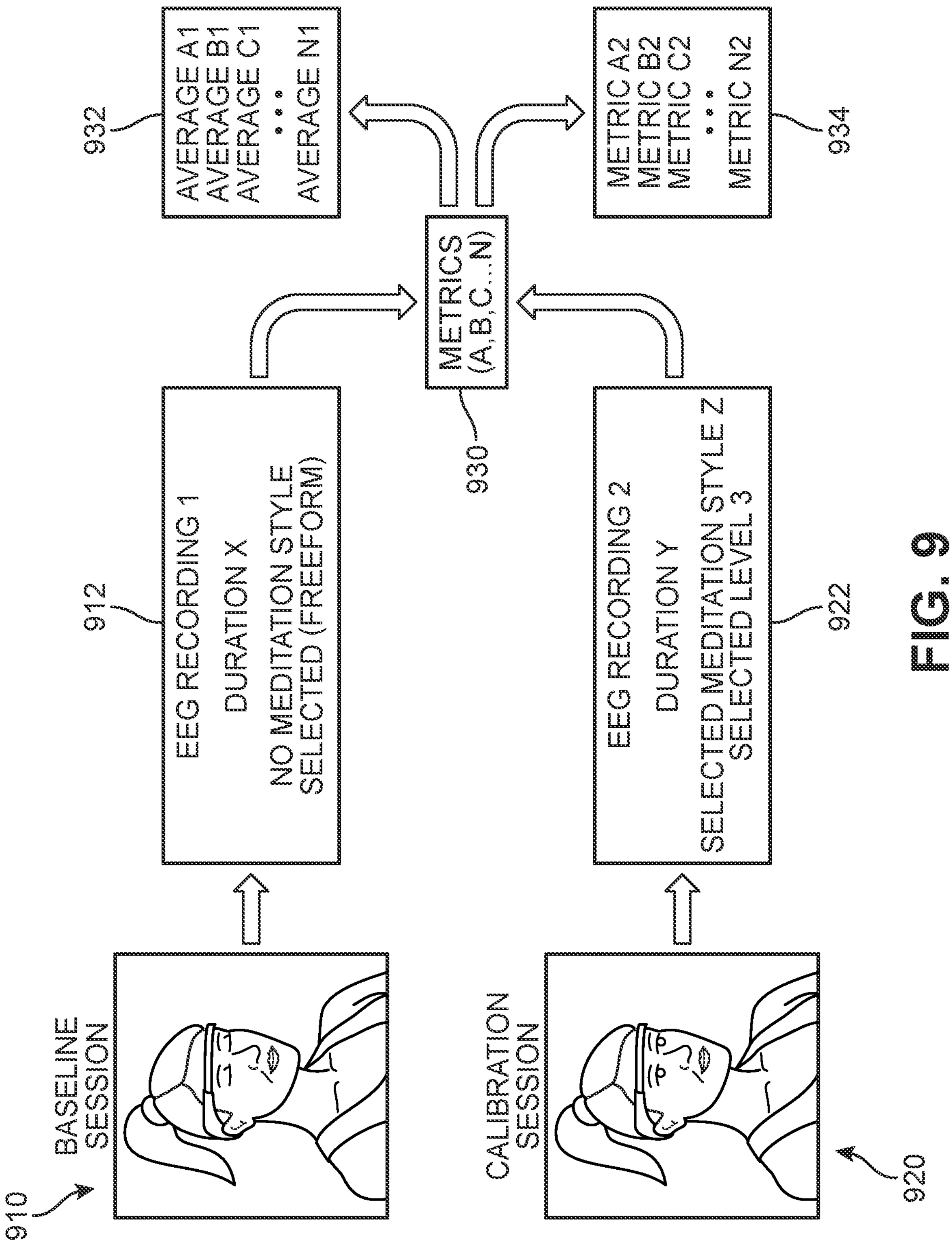
FIGS. 9, 10, and 11 are a sequence of schematic diagrams illustrating a process of generating scores for brainwave activity, according to an embodiment.
Figure 10:
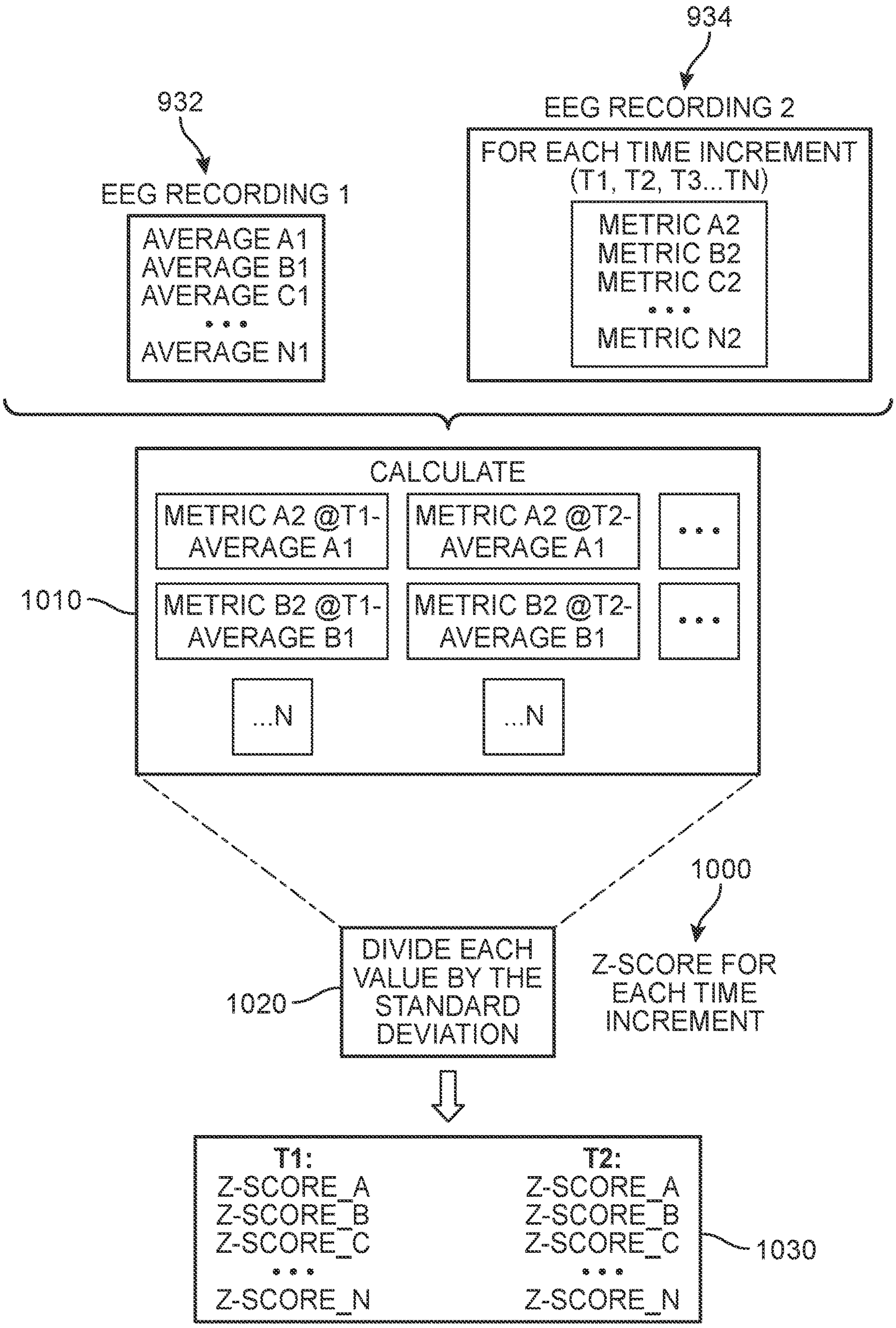
Figure 11:
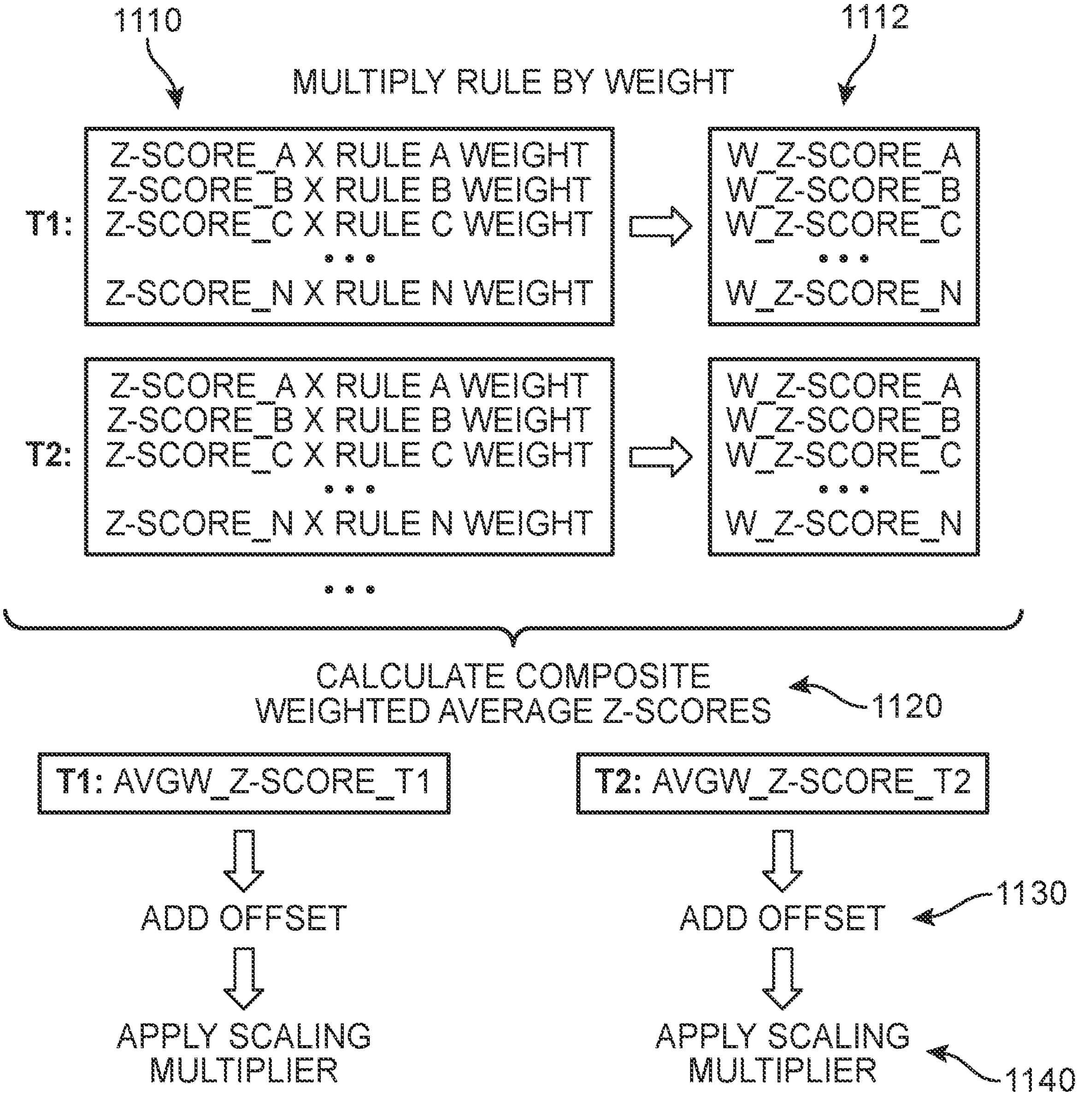

For purposes of clarity to the reader, a sequence of schematic flow diagrams across FIGS. 9, 10, and 11 depicts one example of some of the operations performed by an embodiment of the depth scoring system. Referring first to FIG. 9, a first user is shown engaged in a first session, or a baseline session 910 (eyes closed condition) at a first time, and the same first user is again depicted at a subsequent second time, engaged in a second session, or a calibration session 920. Prior to or after this recording, the system can request inputs regarding the user's (a) level of meditation practice (expertise and familiarity) and (b) meditation goal(s). This information can be used when calculating the user's depth score to better align or the score with the individual's experience and capacity. In one example, an EEG recording for each of the two sessions is recorded, including a first recording 912 and a second recording 922. For the first recording 912, the first user engages in a freeform practice in which the only requirement was that the first user maintain a primarily eyes-closed physical condition. For the second recording 922, during which scoring may be performed, both a meditation style (e.g., "Z") and an experience level (e.g., "Level 3") have been selected by the first user.

In different embodiments, each recording will be received by the depth scoring system. As discussed earlier, metrics representing the baseline session 910 and metrics representing the calibration session 920 can be extracted. In FIG. 9, for purposes of simplicity, descriptor labels for the individual metrics that were calculated such as power, synchrony, etc. are identified by letters (A, B, C . . . N etc.), and the metrics calculated from the first recording 912 are designated by the numeral "1" (e.g., A1, B1, C1, etc.), while the metrics calculated from the second recording 922 are designated by the numeral "2" (e.g., A2, B2, C2, etc.). In one example, the depth scoring system can then determine an average value over the duration X for each metric in the baseline session 910, which has been represented here as Average A1, Average B1, Average C1, . . . Average N1 in a first output 932.

As noted earlier, the depth scoring system can segment the data into equal time-based increments, such as seconds. In some embodiments, for each time increment (e.g., per second), designated as T1, T2, T3, . . . TN for purposes of FIG. 9, the individual metrics are calculated. Thus, at time increment T1, the value for the metric A2 (e.g., coherence) is calculated that can be referred to as A2@T1, and at time increment T2, the value for the metric A2 (e.g., coherence) is again calculated and can be referred to as A2@T2. Similarly, at time increment T1, the value for the metric B2 (e.g., power) is calculated that can be referred to as B2@T1, and at time increment T2, the value for the metric B2 (e.g., power) is again calculated and can be referred to as B2@T2, and so forth for each of the metrics that are available, collectively producing a second output 934.

Moving to FIG. 10, these outputs are then used by the depth scoring system to determine—for each time increment—the user's Z-score for each metric. This is depicted in FIG. 10 by first calculation 1010 and second calculation 1020. At the first calculation 1010, for each value from the second output 934 (e.g., A2@T1, A2@T2, A2@T3, etc. and B2@T1, B2@T2, B2@T3, etc. and so forth) the corresponding average value and/or standard deviation for that metric (taken from first output 932) is subtracted. The result is then divided by the value of the standard deviation that was calculated by the statistical processor for the baseline, and a group of Z-score values for each metric is obtained in a third output 1030. In some embodiments, the Z-scores of third output 1030 can be generated in an ongoing operation, such that a set of Z-scores for a first time increment (e.g., T1) is obtained, and as more data is received during the calibration session, a set of Z-scores for a subsequent second time increment (e.g., T2) is obtained, and so forth. Thus, there will be additional sets of Z-scores obtained as additional time increments of EEG data are received by the depth scoring system.

The next stage of the scoring process is shown in FIG. 11. In this case, each Z-score in a set of Z-scores (at each time increment T1, T2, etc.) is multiplied by the weight assigned to the rule created for the associated metric in a third calculation 1110 to obtain, for each time increment, a set of weighted Z-scores in an ongoing fourth output 1112. Thus, a first Z-score (i.e., at T1) for metric A is multiplied by the weight for Rule "A" that was created based on that metric, a second Z-score (i.e., at T2) for metric A is also multiplied by the weight for Rule "A" that was created based on that metric, and so forth. Similarly, a first Z-score (i.e., at T1) for metric B is multiplied by the weight for Rule "B" that was created based on that metric, a second Z-score (i.e., at T2) for metric B is also multiplied by the weight for Rule "B" that was created based on that metric, and so forth.

In some embodiments, the weighted Z-scores can then be used in a fourth calculation 1120 in which a composite weighted average Z-score 1120 is obtained for that time increment. In this example, for the first time increment T1, based on all of the weighted Z-scores for T1 in the fourth output 1112, an average is calculated ("AVGW_Z-SCORE_T1") that becomes the basis for score assigned to that time increment. Similarly, for the second time increment T2, based on all of the weighted Z-scores for T2 in the fourth output 1112, an average is calculated ("AVGW_Z-SCORE_T2") that becomes the basis for score assigned to the next time increment, and so forth. In some embodiments, an offset is also applied to the composite weighted average Z-score in an offset operation 1130. As noted earlier, an offset is selected and applied in order to shift or move the lowest of the composite weighted average Z-scores to zero, thereby improving readability and simplifying scoring presentation to the user. Similarly, in some embodiments, a scaling multiplier can also be applied to the composite weighted average Z-score in a scaling operation 1140 to shift the highest of the composite weighted average Z-scores to the designated maximum in the range. In other words, an offset helps to define or bound the lowest score and the multiplier helps define or bound the largest score in the range so that the score falls between two pre-set values. It can be appreciated that the offset should be applied first in order to ensure that the lowest end is held at zero. Thus, when the multiplier is subsequently applied, the lowest end of the range (zero) does not change because zero times a multiplier remains zero, while the highest end of the range is shifted to the desired outermost value. The final output can then represent the user's depth score for that period of their meditation and presented to the user or otherwise used to generate visual, audio, and/or haptic feedback and guidance and promote their desired brain state.

Thus, in contrast to conventional neurofeedback one-size-fits-all approaches, the proposed scoring paradigm adapts a person's depth score to each user's (a) level of meditation practice (expertise and familiarity) and (b) meditation goal(s) to provide a personalized training/guidance experience. Rather than simply compare the z-score value to a standard reference set based on normalized metrics for a population to promote one type of brain state, the proposed embodiments allow the user to select a specific brain training goal that may not be normal relative to the population (i.e., that targets their selected state) and helps them move to the desired non-normal state by the presentation of custom-calculated real-time depth scores. As described above, the system can establish a custom reward threshold for each user based on the two brain activity records (reference data during user rest condition+meditative training data when the same user is trying to attain their goal state). Furthermore, in different embodiments, this reward threshold can be adjustable by the user to fine-tune the frequency of reward feedback being generated during their practice. In other words, the proposed systems allow a user to interact with the reward threshold settings (e.g., via the user interface for the app) and either increase the threshold to increase difficulty and reduce the frequency of reward/positive feedback, or decrease the threshold to decrease difficulty and increase the frequency of reward/positive feedback.

In some embodiments (not shown in the drawings), the scoring system can further include a customized reward rate calculator module. The customized reward rate calculator module dynamically responds to an individual user's reward preferences, the selected protocol/rule, and the user's inputted experience level/type. Thus, even if two people use the system and somehow had identical brain waves, if the first person had indicated a first experience level and the second person had indicated a second (different experience level) the two would receive different feedback. Furthermore, in some embodiments, the scoring system enables the user to shift their neurofeedback threshold to maximize their own learning. A user can, for example, identify the reward rate that best suits their learning style (e.g., average of five reward presentations per minute, or average of one reward presentation per minute, or at least 20% of the meditation should be rewarded, etc.). The scoring system can then scan the sample meditation and calculate the reward threshold 'depth' that would create the targeted reward rate. In one embodiment, the scoring system can sort all of the user's depth scores (based on the composite weighted average z-scores, as described above) from lowest to highest, and then determines which depth score matches the user-selected reward percentage or reward rate of the depth scores from the bottom. This is highly desirable because beginner meditators typically need the highest reward rate (reinforcement) because they are so easily discouraged when starting a meditation practice. Thus, they are bolstered by a high reward rate to reassure them that they are on the right track, even though they feel their mind wandering a lot. On the other hand, expert meditators are usually best reinforced by a reward rate of 50% because that is the most sensitive indicator of whether one is "in the zone" (i.e., attaining the target brain state) or not. For example, with expert meditators, a "red zone" (indicating the person is not on the right track, or is otherwise moving outside their target brain state) can be set at approximately 50%, such that around 50% of the non-reward zone scores are in the red zone and the other 50% are in the green zone. However, a 50% reward rate is generally too low a reward rate for most people, especially beginners. The scoring system can thereby accommodate the needs of people with different experience levels by responsively adjusting the reinforcement threshold.

In some embodiments, the user can more explicitly identify their desired reward rate via one or more reward levels shown via the app, regardless of their experience level. For example, the app can present a set of reward levels, each level corresponding to a progressively harder-to-reach standard for each level of expertise. As a non-limiting example, a Level 1 threshold would target an 80% reward rate (the user will be shown feedback that they are "in the green zone" for approximately 80% of their session), a Level 2 threshold would target a 70% reward rate, a Level 3 threshold would target a 60% reward rate, and a Level 4 threshold would target a 50% reward rate. By enabling an adjustable threshold, users can find the neurofeedback experience that best suits their personal style of learning and reinforcement, thereby significantly reducing the number of users who may be discouraged by the too-low rate of reward-feedback, or users who may be stultified or otherwise feel like their practice is stagnant by the too-frequent rate of reward-feedback.

In one embodiment, the scoring system can provide users with an interactive adjustable slider that is overlaid on their brain activity waveform in real-time. The slider can be moved up or down (e.g., by a finger drag on the graphical slider element presented on the device screen in the case of a touchscreen interface) before or during the session to allow the user to quickly personalize their flow state by adjusting the proportion by which their brain activity will more likely fall in the "green zone" versus the "red zone". In addition, it can be appreciated that as an individual user improves in their practice to a desired brain state over time, they will likely need to lower their reward rate to maintain their optimal reward rate (i.e., the brain activity will begin to increasingly shift to the green zone as they become better at their selected meditation). In one option, the user can then interact with the app-provided slider option in an upward direction to move the rewards threshold higher and require better depth scores to fall in the green zone. As another option, the user can simply terminate their practice and re-calibrate so that it aligns with their current level of expertise. The recalibration should create a higher reward threshold that represents the person's now-improved or (greater) level of average depth. In still another option, the user might instead terminate the current protocol and start anew with a selection via the app of a more difficult level of expertise with the same meditation style.

Figure 12:
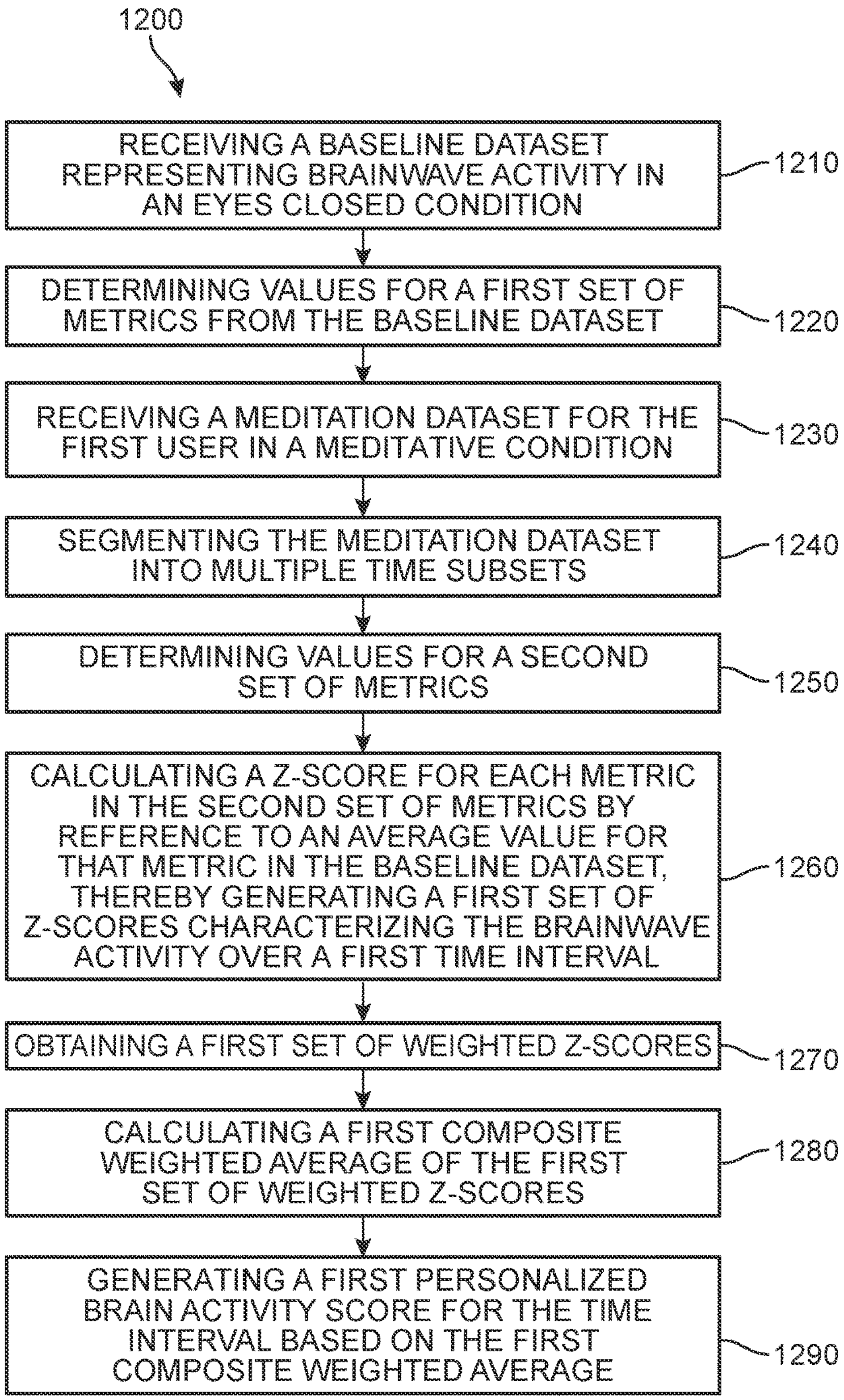
FIG. 12 is a flow chart of a process of evaluating and scoring brain activity, according to an embodiment.

FIG. 12 is a flow chart illustrating an embodiment of a method 1200 for evaluating and scoring brain activity. The method includes a first step 1210 of receiving, at a depth scoring system, a baseline dataset representing brainwave activity for a first user in an eyes closed condition over a first time period, and a second step 1220 of automatically determining, by the depth scoring system and for the baseline dataset, values for a first set of metrics. This method can also include a third step 1230 of receiving, at the depth scoring system, a meditation dataset representing brainwave activity for the first user in a meditative condition over a second time period, and a fourth step 1240 of automatically segmenting, at the depth scoring system and by regular time intervals, the meditation dataset into multiple subsets that includes a first subset, the first subset corresponding to brainwave activity over a first time interval. In addition, the method 1200 can also include a fifth step 1250 of automatically determining, by the depth scoring system and for the first subset, values for a second set of metrics, and a sixth step 1260 of automatically calculating, at the depth scoring system and for the first subset, a z-score for each metric in the second set of metrics by reference to an average value and/or standard deviation for that metric in the baseline dataset, thereby generating a first set of z-scores characterizing the brainwave activity over the first time interval. Finally, the method 1200 can include a seventh step 1270 of obtaining a first set of weighted z-scores by automatically applying, to each z-score in the first set of z-scores, a first weight that is selected by the depth scoring system based on a first meditation style selected by the first user for practice during the second time period, and an eighth step 1280 of automatically calculating, at the depth scoring system, a first composite weighted average of the first set of weighted z-scores, and generating a first personalized brain activity score for the first time interval based on the first composite weighted average.

In other embodiments, the method may include additional steps or aspects. For example, this method can also include automatically providing, via an application associated with the depth scoring system, a first brain activity training session based on a first protocol that is configured to promote the first meditation style, where the meditation dataset is collected as part of the first brain activity training session. In some embodiments, the method can also include steps of receiving, via the application and at the depth scoring system, a user request to engage in the first meditation style during the first brain activity training session, and automatically selecting, by the depth scoring system, the first protocol based on the user selection of the first option. In one example, the first set of z-scores includes a first z-score derived for a value of a first metric of the second set of metrics over the first time interval, and the method can also include steps of automatically identifying a first rule associated with the first protocol that is based on the first metric, and selecting the first weight based on the first weight being assigned to the first rule. In some embodiments, the method also includes automatically applying a scaling multiplier to the first composite weighted average. In another embodiment, each metric in the first set of metrics and/or the second set of metrics represents (e.g., for a given bandwidth) one of power, percent of total power, power ratio, coherence, connectivity, minimum frequency, maximum frequency, phase synchrony, complexity, brain location, and target brainwave direction.

In different embodiments, another system for evaluating and scoring brain activity is disclosed. The system includes a processor and machine-readable media including instructions which, when executed by the processor, cause the processor to perform some or all of the steps described above.

Other methods may be contemplated within the scope of the present disclosure. For example, in some embodiments, a method for evaluating and scoring brain activity is disclosed. The method can include a first step of receiving, at a depth scoring system, a baseline dataset representing brainwave activity for a first user in an eyes closed condition over a first time period, and a second step of automatically determining, by the depth scoring system and for the baseline dataset, values for a first set of metrics. Each metric in the first set of metrics can represent (e.g., for a specific EEG bandwidth) one of power, percent of total power, power ratio, coherence, connectivity, minimum frequency, maximum frequency, phase synchrony, complexity, brain location, and target brainwave direction, among other metrics. A third step can include automatically providing, via an application associated with the depth scoring system, a first brain activity training session based on a first protocol that is configured to promote a first meditation style, and a fourth step can include receiving, via the application, a meditation dataset representing brainwave activity for the first user captured during the first brain activity training session over a second time period. A fifth step can include automatically segmenting, at the depth scoring system and by regular time intervals, the meditation dataset into multiple subsets that can include a first subset, the first subset corresponding to brainwave activity over a first time interval. In addition, a sixth step can include automatically determining, by the depth scoring system and for the first subset, values for a second set of metrics, where each metric in the second set of metrics can represent (e.g., for a specific EEG bandwidth) one of power, percent of total power, power ratio, coherence, connectivity, minimum frequency, maximum frequency, phase synchrony, complexity, brain location, and target brainwave direction, among other metrics. A seventh step can include automatically calculating, at the depth scoring system and for the first subset, a z-score for each metric in the second set of metrics by reference to an average value and/or standard deviation for that metric in the baseline dataset, thereby automatically generating a first set of z-scores characterizing the brainwave activity over the first time interval, and an eighth step can include obtaining a first set of weighted z-scores by applying, to each z-score in the first set of z-scores, a first weight selected from one or more rule weights associated with the first protocol. A ninth step can include automatically calculating, at the depth scoring system, a first composite weighted average of the first set of weighted z-scores, and a tenth step can include automatically presenting, via the application, a first personalized brain activity score for the time interval based on the first composite weighted average.

In other embodiments, the method may include additional steps or aspects. For example, in cases where the first set of z-scores includes a first z-score derived for a value for a first metric of the second set of metrics over the first interval, the method can also include steps of automatically identifying a first rule associated with the first protocol that is based on the first metric, and selecting the first weight from the one or more rule weights based on the first weight being assigned to the first rule. In some embodiments, the method can further include automatically adding an offset to the first composite weighted average to shift the value of the score to zero (in cases where the first composite weighted average corresponds to the lowest score). In another example, the method can include automatically applying a scaling multiplier to the first composite weighted average. In one embodiment, the scaling multiplier converts the first personalized brain activity score into a number falling on a scale between 1 and 1000, such that all scores can be distributed over that range for easy comprehension by the end-users. In some embodiments, the method also includes steps of automatically presenting, via a user interface of the application, options including a first option to engage in the first meditation style based on the first protocol and a second option to engage in a second meditation style based on a second protocol, receiving, via the application and at the depth scoring system, a user selection of the first option, and automatically selecting, by the depth scoring system, the first protocol based on the user selection of the first option. In some embodiments, the z-scores can be used to present feedback to the user via a scoring dashboard for an app shown during their practice. The z-scores can be presented in combination with the adjustable slider described above to modify the rewards threshold.

In another embodiment, a system for evaluating and scoring brain activity is disclosed. The system includes a processor and machine-readable media including instructions which, when executed by the processor, cause the processor to perform some or all of the steps described above.

It can be appreciated that while there are multiple avenues for mediation practice that have been identified (e.g., the various Modern Meditations, Tradition-Based Meditations, Vajrayana Meditations, and Transcendental Meditations, among others) and can be researched to provide target data for the protocol development system described earlier, in some cases, there are brain states that are outside of the realm of standard meditation experiences. In other words, just as each person's neuropsychological profile can be complex and individualized, their brain activity when experiencing their own personalized ideal brain state can be similarly complex and individualized. In cases where a person may desire to attain a target brain state that is outside of the standard meditation practices that are available, tailored feedback that guides them to their own goals can become even more significant.

Figure 13:
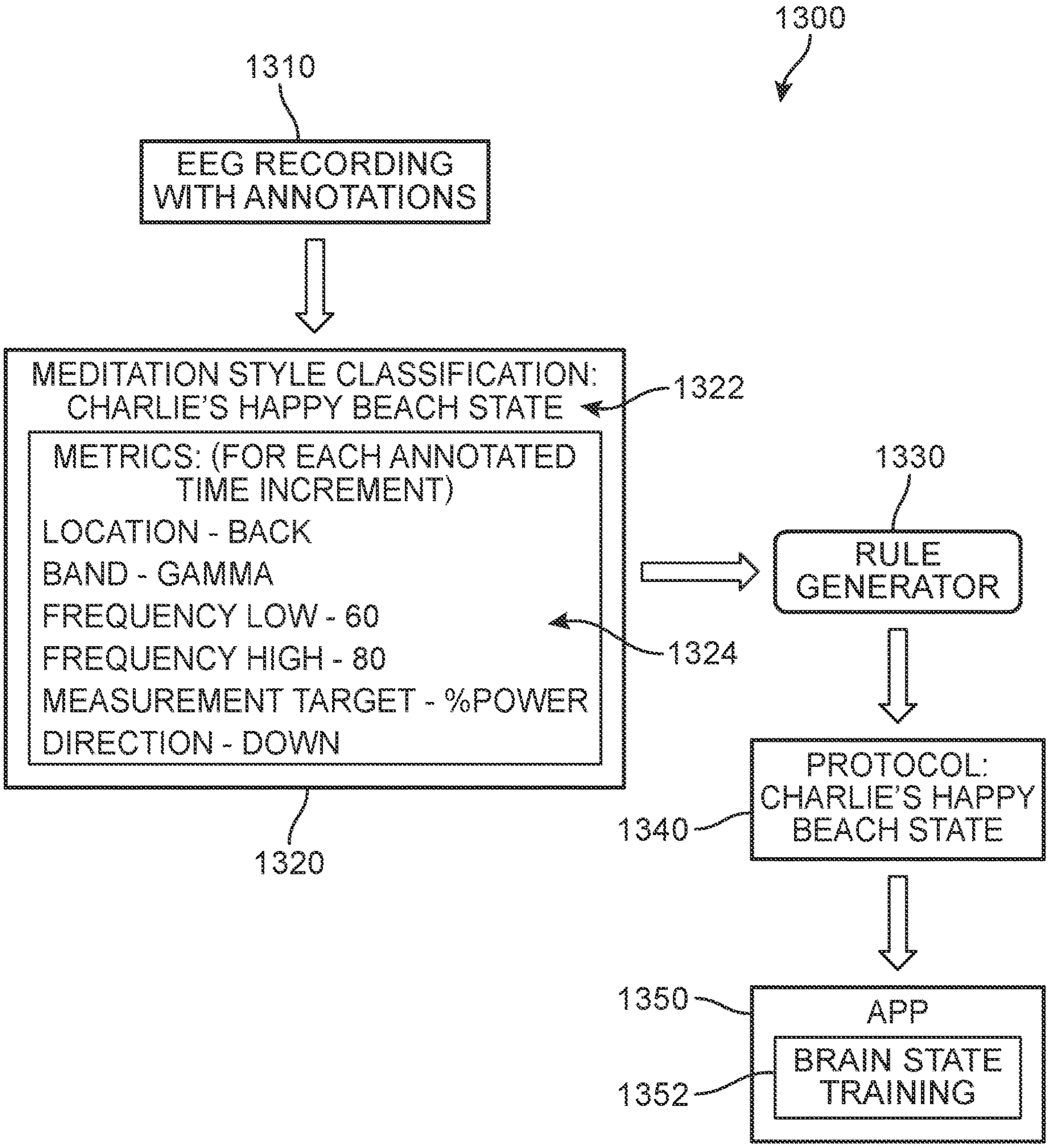
FIG. 13 depicts an overview of a process of developing customized protocols based on individual brainwave data and experience levels, according to an embodiment.

In different embodiments, the proposed systems and methods can include an alternate "custom" protocol development process that can automatically create a brain training protocol for attaining a particular brain state that is based on one or more individual's recorded brain activity data and associated annotations. For purposes of introduction, an example of an overview of a custom protocol development process 1300 is presented with reference to FIG. 13. In FIG. 13, input 1310 in the form of a person's EEG recording (including annotations provided by the same person) can be obtained by the system. As a general matter, user annotations include real-time or near-real-time user inputted descriptors regarding their ongoing brain state recording experience, and will be discussed in greater detail below.

In some embodiments, as shown in FIG. 13, the process 1300 can initially involve processing and extraction of pertinent features from the EEG data, and corresponding metrics 1324, for each time increment directly preceding the user's annotation. These metrics 1324 can be classified and stored in association with the user's EEG recording under their own personalized brain state (e.g., "Charlie's Beach Happy State") that can represent a reference for a desired brain state that they want to pursue in their practice. In some embodiments, the user can also indicate what they believe is the experience level that should be assigned to this data, which can also be linked to the record. One or more of the metrics 1324 are received by a rule generator 1330 of the system, and for each metric, a rule is generated that will be added to a new protocol 1340 for the person (or for someone else's use if they wish to emulate the first person's brain activity). In different embodiments, each metric identified in metrics 1324 (including, for example, brain activity location, bandwidth, low frequency end, high frequency end, measurement category, and oscillation direction, among others, as discussed above with reference to FIG. 3) can be used to automatically generate a rule, via the rule generator 1330, for the custom protocol 1340 that is configured to target the user's brain activity that was identified as optimal based on their annotations. Once the protocol 1340 has been created, the protocol 1340 can be made available to and accessed by an application ("app") 1350 for subsequent braining state training sessions 1352 by application end-users for promotion of this custom/unique brain state. In some embodiments, multiple individual EEG recordings and annotations can be collected from the same person or from a group of persons who practice a single brain state style at the same level of experience to create a new custom protocol.

Figure 14A:
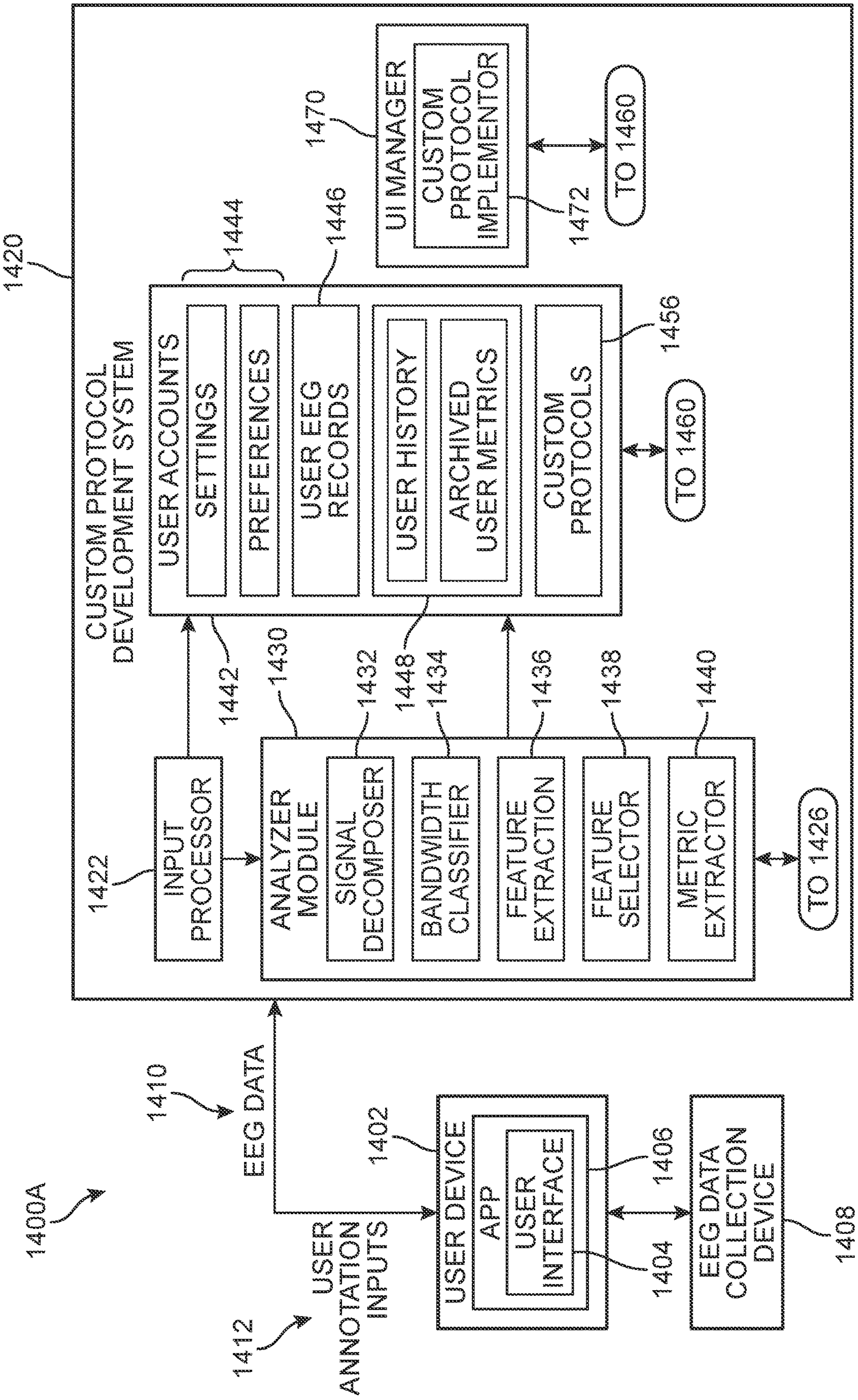
FIGS. 14A and 14B are a schematic diagram of an environment for implementing a custom brain state protocol development system, according to an embodiment.
Figure 14B:
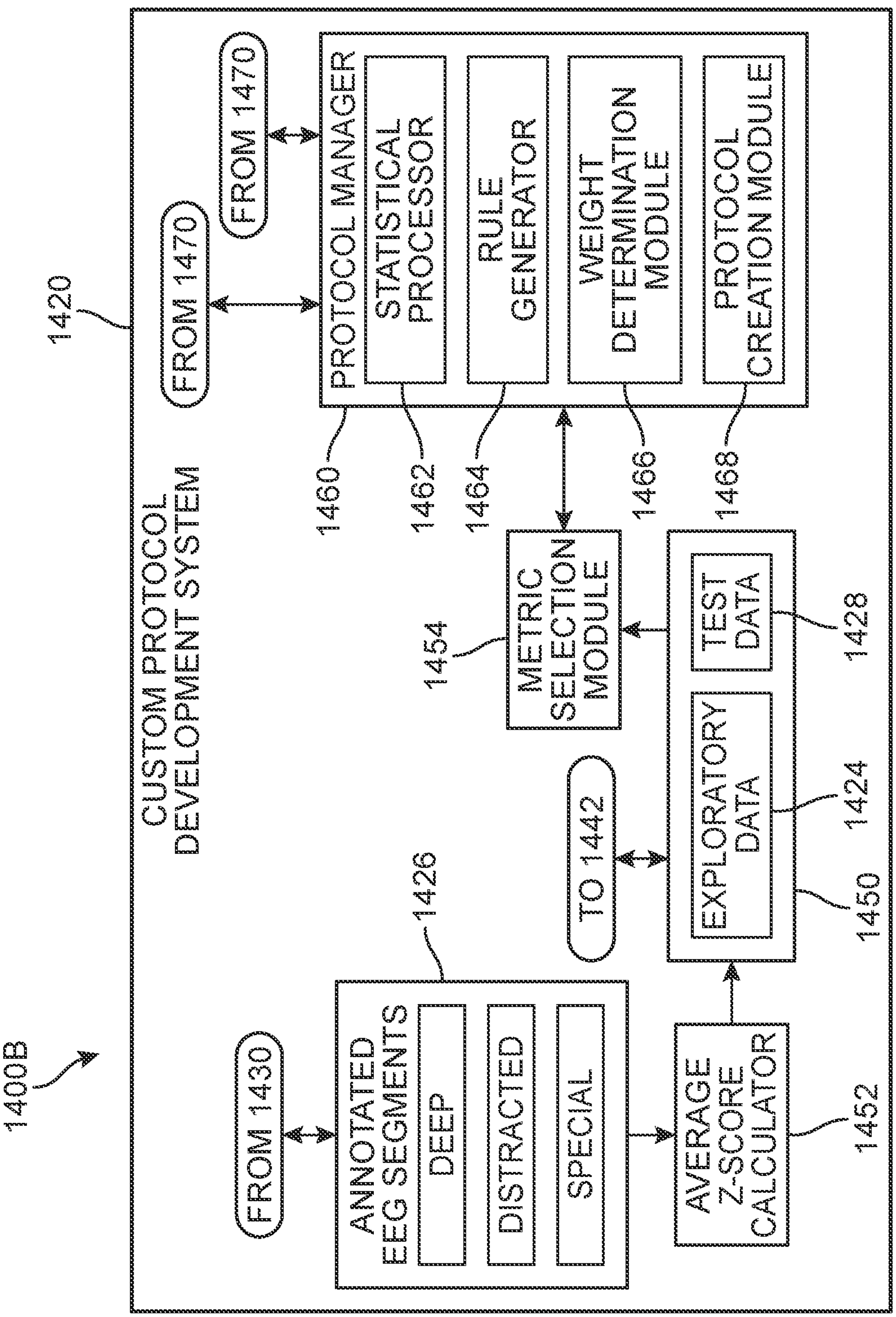

In order to provide the reader with a greater appreciation of these embodiments, FIGS. 14A and 14B depict an overview of an embodiment of an environment 1400 for implementation of a custom protocol development system ("system") 1420 configured to provide customized brain state training and guidance experiences, as described herein. In some embodiments, the system 1420 can also be referred to as a custom rule generation system. In different embodiments, the system 1420 is configured to receive EEG data 1410 along with real- or near-real-time user annotation inputs ("annotations") 1412 describing their perceived mental state during collection of the EEG data 1410. For example, in different embodiments, a user interface 1406 for a custom protocol development and brain training application ("app") 1404 running on a user computing device ("user device") 1402 can be in communication with an EEG or other brain-activity collection device 1408 via a wired or wireless connection. In different embodiments, the user device 1402 and/or other collection device 1408 can also be configured to communicate with the system 1420 over one or more network connections. Thus, in some embodiments, the various components of environment 1400 can be accessed or share information over a cloud network and/or stored on a cloud-based server, while in other embodiments some or all components described herein (including some or all modules of system 1420) can reside locally in the user device and/or a remote server.

In different embodiments, networks could include one or more Wide Area Networks (WANs), Wi-Fi networks, Bluetooth or other Personal Area Networks, cellular networks, as well as other kinds of networks. It may be appreciated that different devices could communicate using different networks and/or communication protocols. The devices can include computing or smart devices as well as more simple IoT devices configured with a communications module/interface and a sensor. The communication module may include a wireless connection using Bluetooth® radio technology, communication protocols described in IEEE 802.11 (including any IEEE 802.11 revisions), Cellular technology (such as GSM, CDMA, UMTS, EV-DO, WiMAX, or LTE), or Zigbee® technology, among other possibilities. In many cases, the communication module is a wireless connection; however, wired connections may also be used. For example, the communication module may include a wired serial bus such as a universal serial bus or a parallel bus, among other connections. In addition, each client device can include provisions for communicating with, and processing information from, system 1420. Each device may include one or more processors and memory. Memory may comprise a non-transitory computer readable medium. Instructions stored within memory may be executed by the one or more processors.

Thus, in different embodiments, user data such as EEG data 1410 obtained via collection device 1408 from the user during a data collection session can be received by system 1420, whether the system 1420 resides locally at the user device 1402 or remotely over a network connection. In one example, an input processor 1422 can receive the user data and prepare the data for use by the system 1420. It should be appreciated that the EEG data 1410 can initially present as raw brain data, typically a complex waveform including brainwaves as well as artifacts such as electrical activity of nearby muscles, electrode motion interference, and/or ambient noise. Thus, in some embodiments, input processor 1422 can be configured to ensure the data is filtered and pre-processed, and/or made ready for further analysis by down-sampling, bandpass filtering, epoch of the data and removal of noisy epochs, removal of noisy components, general artifact rejection/suppression, etc. For example, in one embodiment, a proposed pre-processing pipeline can include several general stages, including filtering, an adaptive technique for artifact removal, interpolation, and independent component analysis (ICA) to remove the artifactual components.

In some embodiments, the pre-processed user data can then be received by an analyzer module 1430. In some embodiments, a signal decomposer module 1432 can perform extraction and separation of signal components from the composite signals and further clean the data for use by the other modules of the system 1420. In addition, the clean data can be initially segregated or otherwise classified for use by a bandwidth classification model 1434 to determine specific types of information such as but not limited to bandwidth/frequency domain. In some embodiments, a feature extraction operation can initially be performed by a feature extraction module ("feature extractor") 1436.

For example, feature extraction can be performed using power spectral density (PSD) and/or log energy entropy. As a general matter, PSD represents the power distribution into the frequency component of the signal, and the latter describes the amount of information carried by a signal or how much randomness is in the signal. In one example, EEG signals can be transformed into PSD using the Fast Fourier Transform and one-second (or other time increment) hamming windows with sufficient overlap to maintain both temporal and frequency resolution and also to minimize the data loss in the window boundary. In addition, in some embodiments, the bandwidth classifier 1434 can then divide each EEG channel into a plurality of sub-bands based on its frequency range (e.g., Delta, Theta, Alpha, Gamma, and Beta). As noted earlier, each EEG sub-band has a different frequency range, such that the average power spectrum for each sub-band can be calculated and used for further analysis. In some embodiments, for each sub-band, the average power spectral density ratios may also be calculated. As a non-limiting example, the average PSD of the beta band of each electrode in the frontal area can be divided by the alpha band of each electrode into parietal and occipital regions (frontal beta/parietal occipital alpha), beta divided by theta for each EEG electrode (beta/theta), and theta then divided by (alpha+beta) for each EEG electrode theta/(alpha+beta), and so forth for each of the other PSDs across the different sub-bands and locations.

It can be appreciated that feature extraction from PSD and/or log energy entropy of the EEG sub-bands can generate a large number of extracted features. In such instances, data complexity including the data variance can negatively impact the performance and accuracy of the system 1420. Thus, in some optional embodiments, a feature selection module ("feature selector") 1438 can be included to reduce dimensionality, improve the predictive accuracy, and enhance the comprehensibility and usability of the obtained results. As some non-limiting examples, feature selector 1430 can employ one or more feature selection algorithms, such as recursive feature elimination (RFE) and Lasso cross-validation (LassoCV) among others, to choose the most pertinent subset of the original features by automated removal of the irrelevant or redundant features.

In different embodiments, a metric extraction module ("metric extractor") 1440 can calculate and produce a plurality of metrics that can be used when determining which rules will be generated and the value of the weights that will be assigned to each rule. Some examples of the metrics that can be identified were described above with reference to FIG. 3. Thus, in different embodiments, the metric extractor 1440 enables the system 1420 to organize the analyzed data and store values for brain-related metrics including, for each sub-band, power, percent of total power, power ratio, coherence, connectivity, minimum frequency, maximum frequency, phase synchrony, complexity, brain location, and target brainwave direction. In addition, generally metrics can be understood to include (a) changes in power in each of the frequency bands and locations, (b) changes in frequency band power as a percent of total power for the bands and locations, (c) changes in connectivity metrics (coherency & synchrony) across the bands between each locations pair, and (d) changes in complexity metrics across the bands between each locations pair. As a more specific example, the system 1420 can be configured to automatically derive up to 416 metrics, including (a) changes in power in each of 13 frequency bands and 8 locations (13*8=104 tests), (b) changes in frequency band power as a percent of total power for 13 bands and 8 locations (13*8=104 tests), (c) changes in 2 connectivity metrics (coherency & synchrony) in 13 bands between 4 locations pairs (front to front, back to back, left to left, right to right) (2*13*4)=(104 tests), and (d) changes in 2 complexity metrics in 13 bands between 4 locations pairs (front to front, back to back, left to left, right to right) (2*13*4)=(104 tests).

As noted earlier, the system 1420 can also receive annotations 1412 during the recording of EEG data 1410. These annotations 1412 reflect the user's own dynamic sense of depth or sensation as it is perceived by them during their session. In some embodiments, the user interface 1406 for the app 1404 is configured to receive inputs via one or more device input modalities (e.g., touchscreen taps, mouse clicks, auditory feedback/responses/notes recorded by a microphone for their user device 1402, visual indicators captured by a camera for their user device 1402, etc.). These inputs can be recognized by the system 1420 as annotations to the live streaming EEG recording. As some non-limiting examples, the user may be requested to provide ongoing inputs via their touchscreen that indicate whether they are (a) in a deep (meditative) brain state, (b) in a distracted brain state, and (c) experiencing a special, unexpected, out-of-the-ordinary, or otherwise different sensation. In other embodiments, additional and/or other mental conditions can be tagged as they are perceived by the user, such as but not limited to joyful, frustrated, anxious, peaceful, bored, etc., and each of these can be used by the system 1420 to define or re-define the custom protocol's rules.

In order to facilitate a steady EEG recording, these annotative inputs should generally be based on subtle or otherwise non-jarring motions. In one example, the system 1420 can define each type of feedback based on the number of taps on the user interface 1406 (if presented a touchscreen). As a non-limiting example, one tap can reflect the user's perception of a deep brain state, two taps in quick succession can reflect the user's perception of a distracted brain state, and three taps in quick succession can reflect the user's perception of a special brain state. In other embodiments, a user may emit some sound to indicate these same categories, such as simply speaking the word "deep" to reflect the user's perception of a deep brain state, speaking the word "distracted" to reflect the user's perception of a distracted brain state, and speaking the word "special" to reflect the user's perception of a special brain state.

In different embodiments, as each annotation is logged by the system 1420, the portion of the EEG recording directly preceding the submission of that annotation across a predesignated time increment can be linked to that annotation. For example, if a user enters a single tap (e.g., indicating a deep state) during the recording, the system 1420 can recognize that the 10 seconds in the EEG immediately preceding the tap should be assigned a "deep" label. In another example, if the user enters two quick taps (e.g., indicating a distracted state) during the recording, the system 1420 can recognize that the 10 seconds in the EEG immediately preceding the first of the two taps should be assigned a "distracted" label. Similarly, if for example the user enters three quick taps (e.g., indicating a special state) during the recording, the system 1420 can recognize that the 10 seconds in the EEG immediately preceding the first of the three taps should be assigned a "special" label. These three examples are described for purposes of illustration only, and it is to be understood that in different embodiments, the time increment used by the system 1420 may be greater or less than 10 seconds. To compensate for the time required by the human user to perceive their own brain state, as well as the ensuing time needed for the human user to react to their internal perception and provide the system with their input, in some embodiments, it can be appreciated that the time increment preceding that is linked to the annotation should include a minimum period of five seconds.

Thus, in some embodiments, the output of the analyzer module 1430 can be segmented based on the user annotations 1412 that were attached or linked to the EEG data 1410, as described above. For example, in different embodiments, a segmentation module 1426 can filter the output of the analyzer module 1430 to two or more buckets or "perceptual categories" that correspond to the user's perceived mental state. In FIG. 14B, the segmentation module 1426 parses the output into at least three categories including a first category corresponding to metrics and other data points for the EEG data that was described by the user as representing a deep state, a second category corresponding to metrics and other data points for the EEG data that was described by the user as representing a distracted state, and a third category corresponding to metrics and other data points for the EEG data that was described by the user as representing a special state. It can be appreciated that the proportion of EEG data in each bucket (category) can vary based on how many times the user submitted annotations during their recording, and what mental state those annotations indicated. Thus, one bucket may include 7 datasets (or 70 seconds of data if the time increment selected was 10 seconds), another bucket may include 3 datasets (or 30 seconds of data), and the remaining bucket may include 1 dataset (or 10 seconds of data). In some embodiments, some time-portions of the data surrounding these annotated snippets of time may be removed as extraneous or otherwise immaterial because the user did not indicate any particular perception for those periods, and so they do not contribute to the system's deciphering of the EEG recording for purposes of developing a protocol.

In different embodiments, for each category (e.g., deep, distracted, special), the average Z-score for each metric may then be calculated via an average Z-score calculation module 1452. For example, the average Z-score calculation module 1452 can receive one or more buckets of data, each bucket linked a different perceptual category and including one or more datasets that were based on the portions of EEG data tagged by the user as representing that perceptual category. For each metric in each dataset, the average Z-score calculation module 1452 can automatically determine the average Z-score of that metric. Thus, as an example, in cases where the time increment selected was 10 seconds, the average Z-score calculation module 1452 can determine the average Z-score over those 10 seconds for each metric.

In some embodiments, the EEG data, annotations, and the EEG-derived data can also be separated or split into two roughly equal groups by a data splitting module 1450 herein referred to as a test data set ("test data") 1428 and an exploratory data set ("exploratory data") 1424. In some embodiments, these data groups or portions thereof can be stored in a user accounts database 1442.

For example, in different embodiments, the system 1420 includes or is configured to access one or more databases, such as user accounts database 1442. The user accounts database 1442 can include a content library that stores account data related to one or more users. The data may include, for each user, a username, a user profile, user selected settings and preferences 1444 such as feedback thresholds, feedback type designations, brain training audio, language, subscription level, etc. in some embodiments, the settings and preferences 1444 can also include a selection by the user regarding their preferred annotation input modality (e.g., touchscreen, voice, visual, etc.), and/or selections of rules defining the specific input they provide (e.g., what sounds should correspond to what category of perception, how many number of taps should correspond to each category of perception, etc.).

Furthermore, each user account may further include a user EEG record repository 1446 that stores previous EEG data, raw and/or processed, and associated data (e.g., metrics). Additional data for each user, such as their past scores (scoring history), app usage history, and archived user metrics (user historical data 1448) can also be optionally stored in or accessed by user accounts database 1442, as well as a directory/record of all of their custom protocols repository 1456 they have created based at least in part on their own brain data or brain data that was submitted from persons in a group they are associated with. In some embodiments, this information can be retrieved by a UI manager 1470 in response to user requests for account data and/or a description of their past custom protocol designs and data, and allow the user to interact with the protocol rules to update or modify characteristics if so desired, which can be incorporated into the protocol by a protocol manager 1460, as described below.

In different embodiments, the system 1420 can be configured to select a narrower set of metrics for translation into rules for the new (custom) protocol. This winnowing allows the system 1420 to focus primarily on only those metrics that have been deemed statistically significant. For example, a smaller set of 1-10 metrics may be selected via a metric selection module 1454 from the larger set of metrics for which values were calculated by the analyzer module 1430. In one embodiment, a winnowed subset of metrics for the exploratory data 1424 are identified by the metric selection module 1454 and applied to the test data 1428 by a statistical processor 1462 of the protocol manager 1460. In one example, the statistical processor 1462 implements a Bonferroni correction to the metrics in order to identify the metrics that show a statistical significance. In other embodiments, other error rate control techniques can be applied, such as the Holm-Bonferroni method, the Sidak correction, false discovery rate control, etc. Once the statistically significant metrics have been identified, a rule generator can, for each statistically significant metric, generate one rule that will be added to a protocol for the user's targeted brain state via a protocol creation module 1468. In addition, in some embodiments, each rule can be assigned a weight via a weight determination module 1466 that calculates the weight that corresponds to the relative importance or significance of that metric (and bandwidth) in successfully producing the target brain state. For example, in different embodiments, a rule weight can be determined initially as a +1 where the data indicates the metric goes up or increases during this brain state, 0 where the data indicates the metric plays no significant role in this brain state, and −1 where the data indicates the metric goes down or decreases during this brain state. If additional data is received that reinforces the direction for a given metric, the weight can be modified accordingly.

As noted earlier, in some embodiments, the various custom protocols with their associated rules and weights that have been developed for a given user can be stored in a custom protocols repository 1456 for access by user device 1402 and implementation by a custom protocol implementor 1472 via the user's preferred brain training application (which may be the same as app 1404). For example, a user may select a particular brain state protocol that was created using their own brain data via a user interface 1406 presented on their display via the app 1404, and in response the app 1404 can implement the associated protocol from the repository 1456. In some embodiments, the protocols maintained in the repository 1456 can also be stored locally on the user device 1402 for offline access and updated when re-connected to the system 1420.

Furthermore, in different embodiments, a rule that was previously generated for a given protocol may be modified (or updated) as new data is received that can enable a fine-tuning of the brain state targeting experience associated with that protocol. In one embodiment, as subsequent feedback is received (e.g., from the user via user interface 1406), the protocol manager 1460 can adjust weights that were attached to the related rule. In another embodiment, as new data is received with additional EEG recordings and annotations that are characterized as falling under the same brain state goal (e.g., Charlie's happy beach state), protocol manager 1460 can, in response to such changes, automatically modify the existing protocol, thereby maintaining the most up-to-date and effective implementation for attaining that custom brain state. Thus, the protocol manager 1460 can learn over time. For example, the app 1404 may request that the user submit feedback regarding their experience, including whether the proffered protocol was aligned with their intended goals during the current session, or via communications to the user at a later time asking about their experience. Based on the feedback the system can reassess the value of one or more weights and/or rules.

It should be understood that in other implementations, environment 1400 can include additional or fewer modules or can include one or more additional computing devices or related server devices. The modules of environment 1400 can be associated with the various local computing devices and, for example, can be disposed within the computing device. In alternative implementations, the modules of environment 1400 can include independent computing devices that are coupled to, and in data communication with, the local computing devices. As used in this description, the term "module" is intended to include, but is not limited to, one or more computers, processing units, or devices configured to execute one or more software programs that include program code that causes a processing device(s) or unit(s) of the computer to execute one or more functions. Processing units can include one or more processors (e.g., microprocessors or central processing units (CPUs)), graphics processing units (GPUs), application specific integrated circuits (ASICs), or a combination of different processors. In alternative embodiments, systems and modules can each include other computing resources/devices (e.g., cloud-based servers) that provide additional processing options for performing one or more of the machine learning determinations and calculations. The processing units or devices can further include one or more memory units or memory banks. In some implementations, the processing units execute programmed instructions stored in memory to cause system, devices, and modules to perform one or more functions described herein. The memory units/banks can include one or more non-transitory machine-readable storage mediums. The non-transitory machine-readable storage medium can include solid-state memory, magnetic disk, and optical disk, a random-access memory (RAM), a read-only memory (ROM), an erasable programmable read-only memory (e.g., EPROM, EEPROM, or Flash memory), or any other tangible medium capable of storing information.

Figure 15:
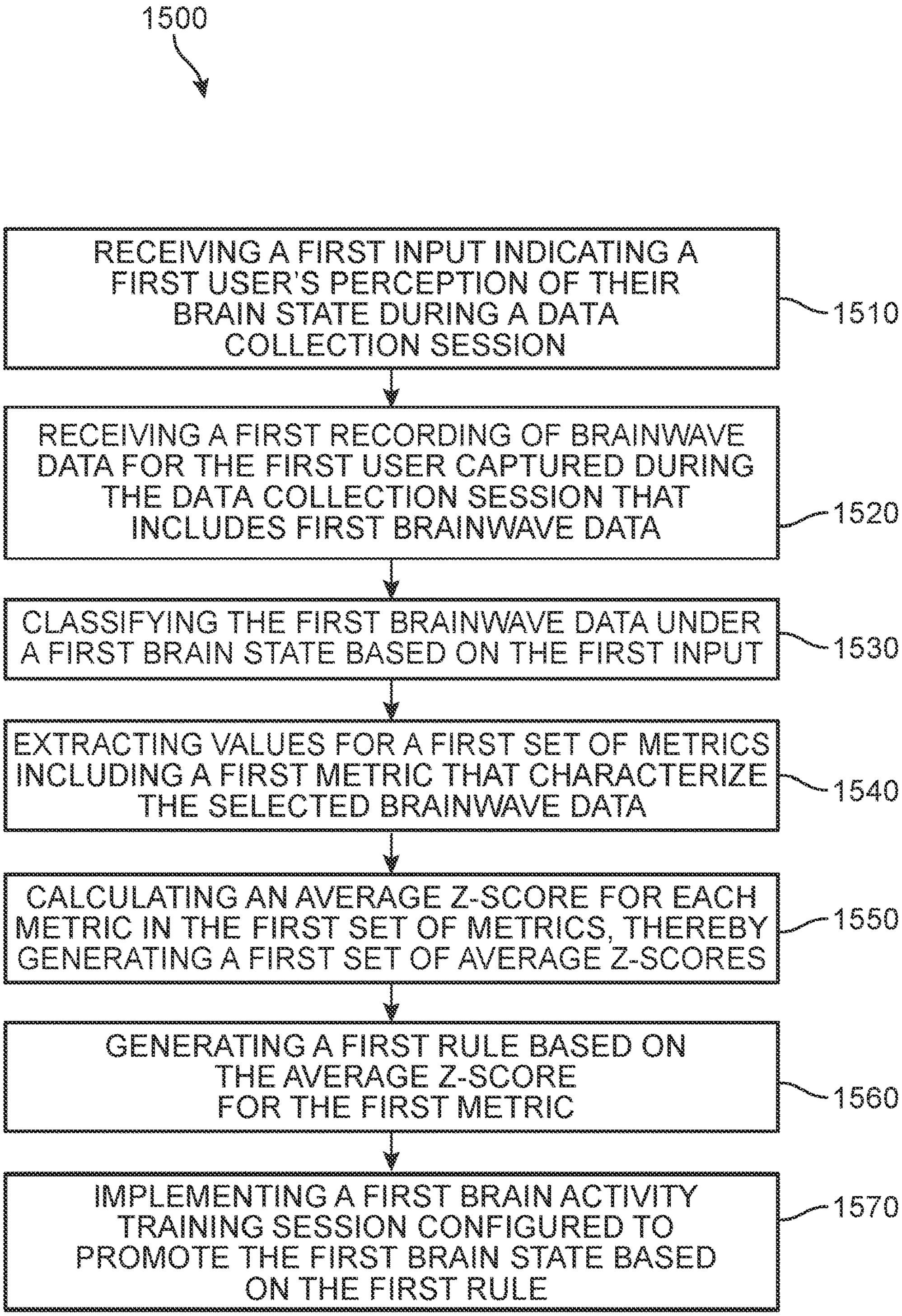
FIG. 15 is a flow chart of a process of intelligent development of customized protocols that promote a specific target brain state, according to an embodiment.

FIG. 15 is a flow chart illustrating an embodiment of a method 1500 for automatically generating rules that promote a specific brain state. This method can include a first step 1510 of receiving from a first user, at a rule generation system, a first input indicating the first user's perception of their brain state during a data collection session and a second step 1520 of receiving, at the rule generation system, a first recording of brainwave data for the first user captured during the data collection session that includes first brainwave data. In addition, the method 1500 can include a third step 1530 of automatically classifying, at the rule generation system, the first brainwave data under a first brain state based on the first input, and a fourth step 1540 of automatically extracting, from the first brainwave data and via the rule generation system, values for a first set of metrics including a first metric that characterize the first brainwave data. Furthermore, the method 1500 may include a fifth step 1550 of automatically calculating, at the rule generation system, an average z-score for each metric in the first set of metrics, thereby generating a first set of average z-scores, a sixth step 1560 of automatically generating, at the rule generation system, a first rule based on the average z-score for the first metric, and a seventh step 1570 of automatically implementing a first brain activity training session configured to promote the first brain state that is based on the first rule.

In other embodiments, the method may include additional steps or aspects. For example, in one embodiment, the first input describes whether the first user experienced one of a deep mental state, a distracted mental state, or a special mental state. In another example, the average z-score for a metric is automatically determined by reference to an average value and/or standard deviation for that metric measured in a previously obtained baseline recording for the first user. In some embodiments, each metric in the first set and/or second set of metrics represents (e.g., for a specific bandwidth) one of power, percent of total power, power ratio, coherence, connectivity, minimum frequency, maximum frequency, phase synchrony, complexity, brain location, and target brainwave direction. In one example, the first input indicates the first user's perception of their brain state over a first period directly preceding their submission of the first input. In some embodiments, the method also includes automatically providing, via an application associated with the rule generation system running on a computing device, the first brain activity training session to a second user.

In addition, in some embodiments, a system for generating rules that promote a specific brain state is disclosed. The system includes a processor and machine-readable media including instructions which, when executed by the processor, cause the processor to perform some or all of the steps described above.

Other methods may be contemplated within the scope of the present disclosure. For example, in some embodiments, a method for automated intelligent development of customized protocols that promote a specific target brain state is disclosed. The method can include a first step of providing to a first user, via an application associated with a protocol development system, a first brain activity collection session, and a second step of receiving from the first user, via the application and at the protocol development system, at a first time during the first brain activity collection session, a first input indicating the first user's perception of their brain state during the first brain activity collection session over a first period directly preceding the first time. A third step can include receiving, via the application and at the protocol development system, a first recording of brainwave data for the first user captured during the first brain activity collection session that can include first brainwave data for the first period. A fourth step can include automatically classifying, at the protocol development system, at least the first brainwave data under a first brain state based on the first input, and a fifth step can include automatically selecting, at the protocol development system, all brainwave data in the first recording, including the first brainwave data, that is classified under the first brain state. Furthermore, a sixth step can include automatically extracting, via the protocol development system, values for a first set of metrics including a first metric that characterize the selected brainwave data. Each metric in the first set of metrics can represent (e.g., for a specific EEG bandwidth) one of power, percent of total power, power ratio, coherence, connectivity, minimum frequency, maximum frequency, phase synchrony, complexity, brain location, and target brainwave direction, among other metrics. A seventh step can include automatically calculating, at the protocol development system, an average z-score for each metric in the first set of metrics, thereby generating a first set of average z-scores. In addition, an eighth step can include automatically generating, at the protocol development system, a first rule for a first protocol based on the average z-score for the first metric, and a ninth step can include automatically providing, via the application and based on the first protocol, a first brain activity training session configured to promote the first brain state.

In other embodiments, the method may include additional steps or aspects. In one embodiment, the method also includes receiving from the first user, via the application and at the protocol development system, at a second time during the first brain activity collection session, a second input indicating the first user's perception of their brain state over the second period which directly preceded the second time. In some embodiments, in cases where the first recording also includes second brainwave data for a second period following the first period, the method also includes automatically classifying, based on the second input, the second brainwave data under the first brain state, and the average z-score for each metric is based on both the first brainwave data and the second brainwave data. In one example, the method can also include automatically classifying, based on the second input, the second brainwave data under a second brain state, and the average z-score for each metric excludes the second brainwave data. In another example, the first input describes whether the first user experienced one of a deep mental state, a distracted mental state, or a special mental state. In one embodiment, the average z-score for a metric is automatically determined by reference to an average value and/or standard deviation for that metric measured in a previously obtained baseline recording. In some embodiments, the number of rules in a protocol is automatically limited to a few select metrics for the brainwave data that have been identified as statistically significant.

In some embodiments, a system for intelligent development of customized protocols that promote a specific target brain state is disclosed. The system includes a processor and machine-readable media including instructions which, when executed by the processor, cause the processor to perform some or all of the steps described above.

As described herein, the methods and systems allow for automation to create statistically validated protocols. It can be appreciated the proposed systems and methods can be used for create neuro-feedback based meditation protocols generally, and/or protocols to replicate any desired brain state. Furthermore, the proposed embodiments provide automated and highly accurate systems and methods for achieving desired brain state goals. These protocols enable users to more readily maintain a consistent meditation practice in which there is real-time second-by-second feedback specific to their targets, guiding each person individually to a deeper practice.

The processes and methods of the embodiments described in this detailed description and shown in the figures can be implemented using any kind of computing system having one or more central processing units (CPUs) and/or graphics processing units (GPUs). The processes and methods of the embodiments could also be implemented using special purpose circuitry such as an application specific integrated circuit (ASIC). The processes and methods of the embodiments may also be implemented on computing systems including read only memory (ROM) and/or random access memory (RAM), which may be connected to one or more processing units. Examples of computing systems and devices include, but are not limited to: servers, cellular phones, smart phones, tablet computers, notebook computers, smart watches, smart glasses, e-book readers, laptop or desktop computers, all-in-one computers, as well as various kinds of digital media players.

The processes and methods of the embodiments can be stored as instructions and/or data on non-transitory computer-readable media. The non-transitory computer readable medium may include any suitable computer readable medium, such as a memory, such as RAM, ROM, flash memory, or any other type of memory known in the art. In some embodiments, the non-transitory computer readable medium may include, for example, an electronic storage device, a magnetic storage device, an optical storage device, an electromagnetic storage device, a semiconductor storage device, or any suitable combination of such devices. More specific examples of the non-transitory computer readable medium may include a portable computer diskette, a floppy disk, a hard disk, magnetic disks or tapes, a read-only memory (ROM), a random access memory (RAM), a static random access memory (SRAM), a portable compact disc read-only memory (CD-ROM), an erasable programmable read-only memory (EPROM or Flash memory), electrically erasable programmable read-only memories (EEPROM), a digital versatile disk (DVD and DVD-ROM), a memory stick, other kinds of solid state drives, and any suitable combination of these exemplary media. A non-transitory computer readable medium, as used herein, is not to be construed as being transitory signals, such as radio waves or other freely propagating electromagnetic waves, electromagnetic waves propagating through a waveguide or other transmission media (e.g., light pulses passing through a fiber-optic cable), or electrical signals transmitted through a wire.

Instructions stored on the non-transitory computer readable medium for carrying out operations of the present invention may be instruction-set-architecture (ISA) instructions, assembler instructions, machine instructions, machine dependent instructions, microcode, firmware instructions, configuration data for integrated circuitry, state-setting data, or source code or object code written in any of one or more programming languages, including an object oriented programming language such as Smalltalk, C++, or suitable language, and procedural programming languages, such as the "C" programming language or similar programming languages.

Aspects of the present disclosure are described in association with figures illustrating flowcharts and/or block diagrams of methods, apparatus (systems), and computing products. It will be understood that each block of the flowcharts and/or block diagrams can be implemented by computer readable instructions. The flowcharts and block diagrams in the figures illustrate the architecture, functionality, and operation of possible implementations of various disclosed embodiments. Accordingly, each block in the flowchart or block diagrams may represent a module, segment, or portion of instructions. In some implementations, the functions set forth in the figures and claims may occur in an alternative order than listed and/or illustrated.

The embodiments may utilize any kind of network for communication between separate computing systems. A network can comprise any combination of local area networks (LANs) and/or wide area networks (WANs), using both wired and wireless communication systems. A network may use various known communications technologies and/or protocols. Communication technologies can include, but are not limited to: Ethernet, 802.11, worldwide interoperability for microwave access (WiMAX), mobile broadband (such as CDMA, and LTE), digital subscriber line (DSL), cable internet access, satellite broadband, wireless ISP, fiber optic internet, as well as other wired and wireless technologies. Networking protocols used on a network may include transmission control protocol/Internet protocol (TCP/IP), multiprotocol label switching (MPLS), User Datagram Protocol (UDP), hypertext transport protocol (HTTP), hypertext transport protocol secure (HTTPS) and file transfer protocol (FTP) as well as other protocols.

Data exchanged over a network may be represented using technologies and/or formats including hypertext markup language (HTML), extensible markup language (XML), Atom, JavaScript Object Notation (JSON), YAML, as well as other data exchange formats. In addition, information transferred over a network can be encrypted using conventional encryption technologies such as secure sockets layer (SSL), transport layer security (TLS), and Internet Protocol security (Ipsec).

Devices for brain data collection such as EEG can employ any available EEG-recording device such as but not limited to headsets with EEG sensors that are typically located inside a headband to be worn on the head. Many vendors produce consumer-grade EEG headbands, including EEG caps, headbands, or headsets produced by NeuroSky Inc.®, Emotiv Inc.®, Macro Tellect®, Myndplay®, Neeuro®, FocusCalm®, or Interaxon Inc.® (e.g., providers of the Muse® headset), or other consumer-grade EEG recording devices.

Other systems, methods, features, and advantages of the disclosure will be, or will become, apparent to one of ordinary skill in the art upon examination of the following figures and detailed description. It is intended that all such additional systems, methods, features, and advantages be included within this description and this summary, be within the scope of the disclosure, and be protected by the following claims.

While various embodiments are described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature or element of any embodiment may be used in combination with or substituted for any other feature or element in any other embodiment unless specifically restricted.

This disclosure includes and contemplates combinations with features and elements known to the average artisan in the art. The embodiments, features, and elements that have been disclosed may also be combined with any conventional features or elements to form a distinct invention as defined by the claims. Any feature or element of any embodiment may also be combined with features or elements from other inventions to form another distinct invention as defined by the claims. Therefore, it will be understood that any of the features shown and/or discussed in the present disclosure may be implemented singularly or in any suitable combination. Accordingly, the embodiments are not to be restricted except in light of the attached claims and their equivalents. Also, various modifications and changes may be made within the scope of the attached claims.

I claim:

1. A method for generating rules that target brain states of specific meditation styles, the method comprising:

receiving, at a rule generation system for an application installed on a first computing device, a first set of metrics extracted from a first brain activity dataset that includes assorted meditation-specific synaptic activity data for multiple human persons each practicing one of a plurality of meditation styles, wherein the first set of metrics is based on EEG data collected via electrodes positioned on each person's head to acquire data from specific brain anatomy locations including front, back, left, right, and cingulate cortex, and the first set of metrics is extracted by:

removing the artifactual components from each person's EEG data by interpolation and independent component analysis (ICA), decomposing signal components to identify, in each person's EEG data, activity occurring in each of Delta, Theta, Alpha, Gamma, and Beta bandwidths, and extracting, from the decomposed signal components, metrics including one or more of power, percent of total power, power ratio, coherence, connectivity, minimum frequency, maximum frequency, phase synchrony, complexity, brain location, and target brainwave direction that are consistent with successfully producing a brain state associated with one of the plurality of meditation styles;

classifying, at the rule generation system, each metric of the first set of metrics under one meditation style of the specific mediation styles, wherein a first metric is classified under a first meditation style, and the first meditation style is based on one of a Modern meditation, Buddhist meditation, Yogic meditation, and Transcendental meditation;

generating, at the rule generation system, a first rule targeting a brain state associated with the first meditation style that is based on the first metric, the first rule associated with a first weight;

providing, to a first user and via a user interface for the application, a first brain activity training session based on the first rule that is configured to promote the first meditation style via neurofeedback, wherein the first brain activity training session includes a depth scoring user feedback system that is configured to:

segment EEG data received from the first user into multiple subsets that include a first subset corresponding to brainwave activity over a first time interval, extract a second set of features from the first subset using power spectral density (PSD) and log energy entropy, calculate, for second set of features in the first subset, a z-score for the first metric by reference to an average value for that metric in the first brain activity dataset, the z-score characterizing the brainwave activity over the first time interval, and obtain a first depth score for the first user during the first time interval by applying the first weight to the z-score;

receiving, at the application and from an EEG headset worn by the first user, the EEG data for the first user while the first brain activity training session is being provided to the first user; and presenting a time-series graph that depicts, for each subset of the multiple subsets of the EEG data, a corresponding depth score, such that the first subset is presented with the first depth score, and each depth score represents, for its corresponding subset of EEG data first time interval whether the first user is successfully producing a brain state linked to the first meditation style.

2. The method of claim 1, wherein the first meditation style is a Modern meditation that includes one of Awakened Mind, Calm and Relaxed, Creativity, Focus, Mindfulness/Stress Reduction, Open Heart, and Quiet Mind.

3. The method of claim 1, further comprising:
classifying a second metric under a second meditation style that differs from the first meditation style; and
generating, at the rule generation system, a second rule that targets a brain state associated with the second meditation style and is based on the second metric.

4. The method of claim 3, further comprising:
presenting, via the user interface, options including a first option to engage in the first meditation style and a second option to engage in the second meditation style;
receiving, via the application and at the rule generation system, a user selection of the first option; and
selecting, by the rule generation system, the first rule based on the user selection of the first option.

5. The method of claim 3, further comprising:
receiving, at the rule generation system, a second brain activity dataset that includes a second set of metrics reflecting assorted EEG data for multiple human persons each practicing the first meditation style;
classifying, at the rule generation system, a third metric extracted from the second brain activity dataset under the first meditation style; and
generating, at the rule generation system, a third rule also targeting the first brain state that is based on the third metric.

6. The method of claim 1, wherein the first brain activity dataset includes information about each person's experience level when practicing their meditation style, and the method further comprises classifying, at the rule generation system, each metric of the first set of metrics under one of a plurality of experience levels.

7. The method of claim 6, wherein the first metric of the first set of metrics is further classified under a first experience level for the first meditation style, and the method further comprises:
classifying a third metric of the first set of metrics under the first meditation style;
classifying the third metric under a second experience level for the first meditation style that is different from the first experience level; and
generating, at the rule generation system, a third rule targeting a third brain state associated with the first meditation style for users at the second experience level that is based on the third metric.

8. The method of claim 7, further comprising:
presenting, via the user interface, options including a first option to engage in a first experience level for the first meditation style and a second option to engage in a second experience level for the first meditation style; and
receiving, via the user interface and at the rule generation system, a user selection of the first option,
wherein selection of the first rule rather than the third rule is further based on the user selection of the first option.

9. A method for generating rules that promote a specific brain state, the method comprising:
receiving from a first user, at a rule generation system, a first input indicating the first user's perception of their brain state during a data collection session, wherein the first input indicates the first user's perception of their brain state over a first period directly preceding their submission of the first input;
receiving, at the rule generation system, a first EEG data for the first user captured during the data collection session via electrodes positioned on the first user's head to acquire data from specific brain anatomy locations including front, back, left, right, and cingulate cortex;
classifying, at the rule generation system, the first EEG data under a first brain state based on the first input;
extracting, from the first EEG data and via the rule generation system, values for a first set of metrics including a first metric by
removing the artifactual components from each person's EEG data by interpolation and independent component analysis (ICA),
decomposing signal components to identify, in each person's EEG data, activity occurring in each of Delta, Theta, Alpha, Gamma, and Beta bandwidths, and
extracting, from the decomposed signal components, metrics including one or more of power, percent of total power, power ratio, coherence, connectivity, minimum frequency, maximum frequency, phase synchrony, complexity, brain location, and target brainwave direction that are consistent with successfully producing one of the plurality of meditation styles;
segmenting the first EEG data into multiple subsets that include a first subset corresponding to brainwave activity over a first time interval,
calculating, for the first subset, a z-score for the first metric by reference to an average value for the first metric in a previously obtained baseline recording for the first user, the z-score characterizing the brainwave activity over the first time interval,
generating, at the rule generation system, a first rule based on the z-score for the first metric;
providing, via a first computing device and to a second user, a first brain activity training session configured to promote the first brain state that is based on the first rule, wherein the first brain activity training session:
is provided while second EEG data is collected from the second user via an EEG headset worn by the second user and transmitted to the first computing device, and
depicts a visual record of the second EEG data in real-time along with the corresponding depth scores, each depth score indicating for its respective time increment whether the first user is successfully producing a brain state linked to the first brain state based on the first rule.

10. The method of claim 9, wherein the first input describes whether the first user experienced one of a deep mental state, a distracted mental state, or a special mental state.

11. The method of claim 9, further comprising reducing a dimensionality of the extracted features using recursive feature elimination (RFE) to select and remove redundant features.

12. The method of claim 9, wherein the first brain state is a Modern meditation that includes one of Awakened Mind, Calm and Relaxed, Creativity, Focus, Mindfulness/Stress Reduction, Open Heart, and Quiet Mind.

13. The method of claim 9, wherein the visual record includes a live time-series graph showing dynamic depth scores over time.

14. The method of claim 9, further comprising providing, via an application associated with the rule generation system running on a computing device, the first brain activity training session to a second user.

15. The method of claim 1, wherein the first meditation style is a Buddhist Meditation that includes one of Anapana, Jhanas, Kasina, Metta, Samatha, Vipassana/Goenka Body- Scanning, Vipassana/Thought-Watching, Zazen/Focused Awareness, and Zazen/Open Monitoring.

16. The method of claim 1, wherein the first meditation style is a Vajrayana Meditation that includes one of Rigpa, Shamatha, and Yidam.

17. The method of claim 1, wherein the first meditation style is a Yogic Meditation that includes one of Acem, Brahma Kumaris (BK) Raja Yoga, Himalayan Yoga Tradition, Isha Yoga Shoonya, Preksha, Satyananda Yoga/Kaya Sthairyam, and Satyananda Yoga/Japa.

18. The method of claim 9, wherein the first meditation style is a Buddhist Meditation that includes one of Anapana, Jhanas, Kasina, Metta, Samatha, Vipassana/Goenka Body-Scanning, Vipassana/Thought-Watching, Zazen/Focused Awareness, and Zazen/Open Monitoring.

19. The method of claim 9, wherein the first meditation style is a Vajrayana Meditation that includes one of Rigpa, Shamatha, and Yidam.

20. The method of claim 9, wherein the first meditation style is a Yogic Meditation that includes one of Acem, Brahma Kumaris (BK) Raja Yoga, Himalayan Yoga Tradition, Isha Yoga Shoonya, Preksha, Satyananda Yoga/Kaya Sthairyam, and Satyananda Yoga/Japa.

* * * * *